United States Patent
Fernandez-Prieto et al.

(10) Patent No.: US 10,092,489 B2
(45) Date of Patent: Oct. 9, 2018

(54) HYDROPHOBICALLY MODIFIED UREA ETHERS AS STRUCTURANTS FOR HYDROPHOBIC SYSTEMS

(71) Applicant: The Procter & Gamble Company, Cincinnati, OH (US)

(72) Inventors: Susana Fernandez-Prieto, Bennicassim/Castellon (ES); Marc Dolatkhani, Cestas (FR); Wim Michel De Borggraeve, Leuven (BE); Monissa Cuebillas Paderes, Heverlee (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/456,613

(22) Filed: Mar. 13, 2017

(65) Prior Publication Data

US 2017/0258694 A1  Sep. 14, 2017

(30) Foreign Application Priority Data

Mar. 14, 2016 (EP) ..................... 16160129
Oct. 5, 2016 (EP) ..................... 16192347

(51) Int. Cl.

| | | |
|---|---|---|
| *A61K 8/37* | (2006.01) | |
| *A61K 8/04* | (2006.01) | |
| *A61K 8/11* | (2006.01) | |
| *A61K 8/42* | (2006.01) | |
| *A61Q 13/00* | (2006.01) | |
| *A61Q 19/00* | (2006.01) | |
| *C11D 11/00* | (2006.01) | |
| *C11D 17/00* | (2006.01) | |
| *C11D 17/04* | (2006.01) | |
| *C11D 3/00* | (2006.01) | |
| *C11D 3/32* | (2006.01) | |
| *C11D 3/50* | (2006.01) | |
| *A61Q 5/00* | (2006.01) | |
| *A61Q 15/00* | (2006.01) | |
| *A61K 8/86* | (2006.01) | |
| *A61Q 19/10* | (2006.01) | |
| *A61L 9/00* | (2006.01) | |
| *C08G 65/333* | (2006.01) | |
| *C11D 3/37* | (2006.01) | |
| *C08L 71/02* | (2006.01) | |

(52) U.S. Cl.
CPC ............... *A61K 8/37* (2013.01); *A61K 8/042* (2013.01); *A61K 8/11* (2013.01); *A61K 8/42* (2013.01); *A61K 8/86* (2013.01); *A61L 9/00* (2013.01); *A61Q 5/00* (2013.01); *A61Q 13/00* (2013.01); *A61Q 15/00* (2013.01); *A61Q 19/00* (2013.01); *A61Q 19/10* (2013.01); *C08G 65/33351* (2013.01); *C08G 65/33396* (2013.01); *C08L 71/02* (2013.01); *C11D 3/001* (2013.01); *C11D 3/0015* (2013.01); *C11D 3/0068* (2013.01); *C11D 3/323* (2013.01); *C11D 3/3707* (2013.01); *C11D 3/50* (2013.01); *C11D 11/0017* (2013.01); *C11D 11/0023* (2013.01); *C11D 17/0039* (2013.01); *C11D 17/047* (2013.01); *C08G 2650/50* (2013.01)

(58) Field of Classification Search
CPC . A61K 8/37; A61K 8/042; A61K 8/42; A61K 8/11; C11D 3/50; C11D 11/0017; C11D 3/001; C11D 3/0068; C11D 3/323; C11D 11/0023; C11D 17/0039; C11D 17/047; C11D 3/0015; A61C 19/00; A61C 13/00; A61Q 19/00; A61Q 13/00
See application file for complete search history.

(56) References Cited

U.S. PATENT DOCUMENTS

| | | |
|---|---|---|
| 4,110,309 A | 8/1978 | Schulze et al. |
| 5,084,202 A | 1/1992 | Lin et al. |
| 8,450,259 B2 | 5/2013 | Smets et al. |
| 2013/0224139 A1* | 8/2013 | Hong ............... A61K 8/42 424/65 |
| 2013/0303427 A1* | 11/2013 | Fernandez Prieto .. A01N 25/28 510/299 |

FOREIGN PATENT DOCUMENTS

WO WO2013123324A1 A1 8/2013

OTHER PUBLICATIONS

EP Search report for Application No. 16160129.9-1301, dated Sep. 2, 2016, 9 pages.
Patricia Y. W. Dankers et al: 1-12, "Hierarchical Formation of Supramolecular Transient Networks in Water: A Modular Injectable Delivery System", Advanced Materials, vol. 24, No. 20, May 22, 2012 (May 22, 2012), pp. 2703-2709, XP055161851, ISSN: 0935-9648.

* cited by examiner

*Primary Examiner* — Doan T Phan
(74) *Attorney, Agent, or Firm* — Gregory S. Darley-Emerson

(57) ABSTRACT

Consumer product compositions comprising hydrophobically modified urea ethers.

19 Claims, No Drawings

HYDROPHOBICALLY MODIFIED UREA ETHERS AS STRUCTURANTS FOR HYDROPHOBIC SYSTEMS

FIELD OF THE INVENTION

The present invention relates to hydrophobically modified urea ethers, compositions comprising said hydrophobically modified urea ethers and consumer products comprising said compositions.

BACKGROUND OF THE INVENTION

Polyetheramines, well known under the name Tradename of Jeffamine®, contain primary amino groups attached to the end of a polyether backbone. The polyether backbone is normally based on propylene oxide, ethylene oxide or mixtures thereof.

Polyetheramines are well-known as cross-linker for polyureas, as co-reagents in epoxy systems and as corrosion inhibitor.

Surprisingly, it has been found, that introducing some hydrophobic urea functionalities can transform these polyetheramines into efficient rheology modifiers providing not only an increase in viscosity or even gel formation, but also suspension power to hydrophobic systems or hydrophobic benefit agent/composition.

Increasing the viscosity of hydrophobic systems overcomes undesired premature release of the hydrophobic benefit agent/composition or allows tailoring the release profile of the hydrophobic composition. For example, conventional perfume compositions have a pyramid three-tiered structure, which contains a high amount of the so called base notes, an intermediate amount of the middle notes, and a lower amount of the top notes. It is desired to increase the longevity of top notes, which have a fast evaporation profile. By increasing their viscosity through the addition of the hydrophobically modified urea ethers, it is possible to delay the evaporation of the top notes and therefore increase their longevity. It is desired to improve the absorption profile of hydrophobic actives in creams and skin care compositions, by modifying the rheology of such actives compositions. By increasing viscosity with addition of hydrophobic ally modified urea ethers to the hydrophobic actives, retention on skin of the creams and skin care compositions is prolonged and therefore absorption profile.

SUMMARY OF THE INVENTION

The present invention relates to a consumer product composition comprising:
a) a hydrophobic material;
b) from 0.1% to 10% by weight of a hydrophobic ally modified urea ether according to having the following structure:

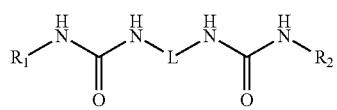
(I)

wherein $R_1$, $R_2$ and L are selected from the group consisting of substituted or unsubstituted aliphatic carbon chain, substituted or unsubstituted polyether chain and mixtures thereof; with the proviso that at least one $R_1$, $R_2$ or L contains an ether moiety;

and wherein the hydrophobically modified urea ether has a molecular weight from 1000 to 7000 Da.

DETAILED DESCRIPTION OF THE INVENTION

Hydrophobically Modified Urea Ethers

The hydrophobically modified urea ether of use in the present consumer product compositions has following structure:

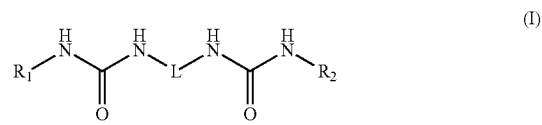
(I)

wherein $R_1$, $R_2$ and L may be selected from the group consisting of substituted or unsubstituted aliphatic carbon chain, substituted or unsubstituted polyether chain and mixtures thereof, with the proviso that at least one $R_1$, $R_2$ or L contains an ether moiety; and the molecular weight is from 1000 Da to 7000 Da, preferably from 1100 Da to 3500 Da, even more preferably from 1100 Da to 3000 Da.

L may have the formula;

$$-A_a-B_b-C_c-D_d- \quad (II)$$

wherein:
a, b, c and d are integers independently selected from 0 to 40 and (a+b+c+d) is from 3 to 132, preferably from 3 to 85

A, B, C, D are independently selected from the group consisting of:

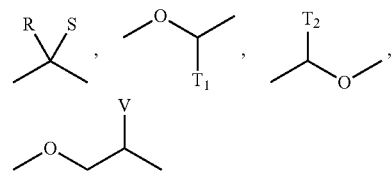

wherein R, S, $T_1$, $T_2$, V are independently selected from the group consisting of:

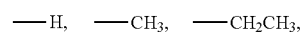

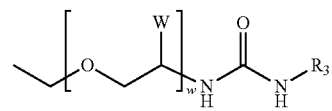

wherein W is —H or —CH$_3$, w is an integer from 1 to 30 and $R_3$ is a substituted or unsubstituted aliphatic carbon chain from 8 to 20 carbons, preferably from 10 to 18.

In one aspect, $R_1$ and $R_2$ are independently selected from the group consisting of:

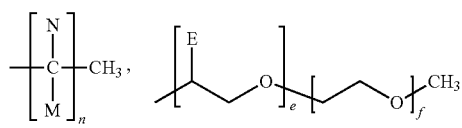

wherein a) N, M and E are independently selected from the group consisting of —H, —CH$_3$, —CH$_2$CH$_3$, preferably, N and M are —H and E is —CH$_3$;
b) n is an integer from 8 to 20, preferably from 10 to 18;
c) e and f are integers independently selected from 0 to 30, and (e+f) is from 1 to 30, preferably (e+f) is from 3 to 15.

R$_1$, R$_2$ and R$_3$ may be the same.

R$_1$, R$_2$ and R$_3$ may comprise the polyether chain. Alternatively L may comprise the polyether chain.

The polyether chain may be partially substituted, in other words, not all available points for substitution are substituted. Preferably, the polyether chain is substituted with methyl groups.

Non-limiting examples of the hydrophobic ally modified urea ether are shown in Table 1. The present invention contemplates any mixture thereof of the examples in Table 1.

TABLE 1

Non-limiting examples of hydrophobically modified urea ethers

| Structure | Molecular weight (Da) | x + z | y | Hydrophobically modified urea ether |
|---|---|---|---|---|
| A | 1191 | ~3.6 | ~9.0 | C$_{18}$H$_{37}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{18}$H$_{37}$ |
| B | 1491 | ~6.0 | ~12.5 | C$_{18}$H$_{37}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{18}$H$_{37}$ |
| C | 2591 | ~6.0 | ~39 | C$_{18}$H$_{37}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{18}$H$_{37}$ |
| D | 1135 | ~3.6 | ~9 | C$_{16}$H$_{33}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{16}$H$_{33}$ |
| E | 1435 | ~6.0 | ~12.5 | C$_{16}$H$_{33}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{16}$H$_{33}$ |
| F | 2535 | ~6.0 | ~39 | C$_{16}$H$_{33}$–NH–C(O)–NH–CH(CH$_3$)–CH$_2$–[O–CH(CH$_3$)–CH$_2$]$_x$–[O–CH$_2$CH$_2$]$_y$–[O–CH$_2$–CH(CH$_3$)]$_z$–NH–C(O)–NH–C$_{16}$H$_{33}$ |

TABLE 1-continued

Non-limiting examples of hydrophobically modified urea ethers

| Structure | Molecular weight (Da) | x + z | y | Hydrophobically modified urea ether |
|---|---|---|---|---|
| G | 2091 | 32 | | $C_{18}H_{33}$—NH—C(O)—NH—CH$_2$CH$_2$CH$_2$—[O—CH$_2$CH$_2$]$_x$—O—CH$_2$CH$_2$CH$_2$—NH—C(O)—NH—$C_{18}H_{37}$ |
| H | 2035 | 32 | | $C_{16}H_{33}$—NH—C(O)—NH—CH$_2$CH$_2$CH$_2$—[O—CH$_2$CH$_2$]$_x$—O—CH$_2$CH$_2$CH$_2$—NH—C(O)—NH—$C_{16}H_{33}$ |
| I | 1326 | | | Trimethylolpropane-based tri-arm structure with $C_{18}H_{37}$ urea end groups; $x + y + z = \sim 5\text{-}6$ |
| J | 1242 | | | Trimethylolpropane-based tri-arm structure with $C_{16}H_{33}$ urea end groups; $x + y + z = \sim 5\text{-}6$ |
| K | 1322 | ~6.0 | ~12.5 | $C_{12}H_{25}$—NH—C(O)—NH—CH(CH$_3$)—[O—CH(CH$_3$)CH$_2$]$_x$—[O—CH$_2$CH$_2$]$_y$—[O—CH$_2$CH(CH$_3$)]$_z$—NH—C(O)—NH—$C_{12}H_{25}$ |
| L | 2252 | 19 | 3 | $H_3C$—[O—CH$_2$CH$_2$]$_x$—[O—CH(CH$_3$)CH$_2$]$_y$—NH—C(O)—NH—(CH$_2$)$_{12}$—NH—C(O)—NH—[CH$_2$CH(CH$_3$)—O]$_y$—[CH$_2$CH$_2$—O]$_x$—$CH_3$ |

The Composition

The consumer product composition according to the present invention comprises:
a) a hydrophobic material
b) from 0.1% to 10% by weight of the hydrophobically modified urea ether of the present invention, preferably from 0.1% to 7% by weight, even more preferably from 0.5% to 5% by weight.

The hydrophobic material may be a perfume raw material, an emollient, a solvent, a sensate and mixtures thereof.

The hydrophobic material may be a perfume composition comprising perfume raw materials, solvents and mixtures thereof.

Without being bound by theory, perfume compositions may be mainly formed by perfume raw materials and they are used to provide a pleasant scent, remove malodors, aromatherapy and combinations thereof. In one aspect, said perfume composition may comprise perfume raw materials listed in Table 2 and mixtures thereof. In one aspect, said perfume raw materials may be used alone. In another aspect, said perfume raw materials may be combined with other ingredients such as eluents.

TABLE 2

Non-limiting examples of perfume raw materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | jasmin lactone | 6-[(E)-pent-2-enyl]oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |

TABLE 2-continued

Non-limiting examples of perfume raw materials

| Item | Common Name | IUPAC Name |
|---|---|---|
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | naphthalen-2-yl-phenylmethanone |
| 93 | decen-1-yl cyclopentanone | 2-[(2E)-3,7-dimethylocta-2,6-dienyl]cyclopentan-1-one |
| 94 | fruity cyclopentanone (veloutone) | 2,2,5-trimethyl-5-pentylcyclopentan-1-one |
| 95 | 4-methoxy-2-methyl butane thiol (blackcurrant mercaptan) | 4-methoxy-2-methylbutane-2-thiol |
| 96 | Grapefruit Mercaptan | 2-(4-methyl-1-cyclohex-3-enyl)propane-2-thiol |
| 97 | Buccoxime | N-(1,5-dimethyl-8-bicyclo[3.2.1]octanylidene)hydroxylamine |
| 98 | Labienoxime | 2,4,4,7-Tetramethyl-6,8-nonadiene-3-one oxime |
| 99 | Undecavertol | (E)-4-methyldec-3-en-5-ol |
| 100 | Decanal diethyl acetal | 1,1-diethoxydecane |
| 101 | Diethyl maleate | diethyl but-2-enedioate |
| 102 | Ethyl Acetoacetate | ethyl 3-oxobutanoate |
| 103 | frutonile | 2-Methyldecanenitrile |
| 104 | Methyl dioxolan | ethyl 2-(2-methyl-1,3-dioxolan-2-yl)acetate |
| 105 | Cetalox | 3a,6,6,9a-tetramethyl-2,4,5,5a,7,8,9,9b-octahydro-1H-benzo[e][1]benzofuran |
| 106 | Cyclopentol | |
| 107 | Delta-damascone | (E)-1-(2,6,6-trimethyl-1-cyclohex-3-enyl)but-2-en-1-one |
| 108 | Eucalyptol | 1,3,3-trimethyl-2-oxabicyclo[2,2,2]octane |
| 109 | Flor acetate | |
| 110 | Ionone gamma methyl | (E)-3-methyl-4-(2,6,6-trimethyl-1-cyclohex-2-enyl)but-3-en-2-one |
| 111 | Laevo trisandol | |
| 112 | Linalool | 3,7-dimethylocta-1,6-dien-3-ol |
| 113 | Violiff | [(4Z)-1-cyclooct-4-enyl]methyl carbonate |
| 114 | Cymal | 3-(4-propan-2-ylphenyl)butanal |
| 115 | Bourgeonal | 3-(4-tert-butylphenyl)propanal |

In one aspect, the perfume composition may comprise perfume raw materials able to mask, mitigate or reduce malodour. In one aspect, said malodor reduction composition or said perfume composition may comprise perfume raw materials listed in Table 3 and mixtures thereof.

TABLE 3

Non-limiting examples of malodor perfume raw materials

| Number | Material Name | CAS Number |
|---|---|---|
| 1 | 2-ethylhexyl (Z)-3-(4-methoxyphenyl)acrylate | 5466-77-3 |
| 2 | 2,4-dimethyl-2-(5,5,8,8-tetramethyl-5,6,7,8-tetrahydronaphthalen-2-yl)-1,3-dioxolane | 131812-67-4 |
| 3 | 1,1-dimethoxynon-2-yne | 13257-44-8 |
| 4 | para-Cymen-8-ol | 1197-01-9 |
| 7 | 3-methoxy-7,7-dimethyl-10-methylenebicyclo[4.3.1]decane | 216970-21-7 |
| 9 | Methoxycyclododecane | 2986-54-1 |
| 10 | 1,1-dimethoxycyclododecane | 950-33-4 |
| 11 | (Z)-tridec-2-enenitrile | 22629-49-8 |
| 13 | Oxybenzone | 131-57-7 |
| 14 | Oxyoctaline formate | 65405-72-3 |
| 16 | 4-methyl-1-oxaspiro[5.5]undecan-4-ol | 57094-40-3 |
| 17 | 7-methyl-2H-benzo[b][1,4]dioxepin-3(4H)-one | 28940-11-6 |
| 18 | 1,8-dioxacycloheptadecan-9-one | 1725-01-5 |
| 21 | 4-(tert-pentyl)cyclohexan-1-one | 16587-71-6 |
| 22 | o-Phenyl anisol | 86-26-0 |
| 23 | 3a,5,6,7,8,8b-hexahydro-2,2,6,6,7,8,8-heptamethyl-4H-indeno(4,5-d)-1,3-dioxole | 823178-41-2 |
| 25 | 7-isopropyl-8,8-dimethyl-6,10-dioxaspiro[4.5]decane | 62406-73-9 |
| 28 | Octyl 2-furoate | 39251-88-2 |
| 29 | Octyl acetate | 112-14-1 |
| 30 | octanal propylene glycol acetal | 74094-61-4 |
| 31 | Octanal | 124-13-0 |
| 32 | Octanal dimethyl acetal | 10022-28-3 |
| 33 | Myrcene | 123-35-3 |
| 34 | Myrcenol | 543-39-5 |
| 35 | Myrcenyl acetate | 1118-39-4 |
| 36 | Myristaldehyde | 124-25-4 |
| 37 | Myristicine | 607-91-0 |
| 38 | Myristyl nitrile | 629-63-0 |
| 39 | 2,2,6,8-tetramethyl-1,2,3,4,4a,5,8,8a-octahydronaphthalen-1-ol | 103614-86-4 |
| 42 | Ocimenol | 5986-38-9 |
| 43 | Ocimenol | 28977-58-4 |
| 47 | Nopyl acetate | 128-51-8 |
| 48 | Nootkatone | 4674-50-4 |
| 49 | Nonyl alcohol | 143-08-8 |
| 50 | Nonaldehyde | 124-19-6 |
| 52 | 12-methyl-14-tetradec-9-enolide | 223104-61-8 |
| 57 | N-ethyl-p-menthane-3-carboxamide | 39711-79-0 |
| 61 | 1-(3-methylbenzofuran-2-yl)ethan-1-one | 23911-56-0 |
| 62 | 2-methoxynaphthalene | 93-04-9 |
| 63 | Nerolidol | 7212-44-4 |
| 64 | Nerol | 106-25-2 |
| 65 | 1-ethyl-3-methoxytricyclo[2.2.1.02,6]heptane | 31996-78-8 |
| 67 | Methyl (E)-non-2-enoate | 111-79-5 |
| 68 | 10-isopropyl-2,7-dimethyl-1-oxaspiro[4.5]deca-3,6-diene | 89079-92-5 |
| 69 | 2-(2-(4-methylcyclohex-3-en-1-yl)propyl)cyclopentan-1-one | 95962-14-4 |
| 70 | Myrtenal | 564-94-3 |
| 71 | (E)-4-(2,2,3,6-tetramethylcyclohexyl)but-3-en-2-one | 54992-90-4 |
| 74 | Myraldyl acetate | 53889-39-7 |
| 75 | Musk tibetine | 145-39-1 |
| 76 | 1,7-dioxacycloheptadecan-8-one | 3391-83-1 |
| 77 | Musk ketone | 81-14-1 |
| 78 | Musk ambrette | 83-66-9 |
| 79 | 3-methylcyclopentadecan-1-one | 541-91-3 |
| 80 | (E)-3-methylcyclopentadec-4-en-1-one | 82356-51-2 |
| 82 | 3-methyl-4-phenylbutan-2-ol | 56836-93-2 |
| 83 | 1-(4-isopropylcyclohexyl)ethan-1-01 | 63767-86-2 |
| 85 | Milk Lactone | 72881-27-5 |

TABLE 3-continued

Non-limiting examples of malodor perfume raw materials

| Number | Material Name | CAS Number |
|---|---|---|
| 91 | Methyl octine carbonate | 111-80-8 |
| 92 | Methyl octyl acetaldehyde | 19009-56-4 |
| 93 | 6,6-dimethoxy-2,5,5-trimethylhex-2-ene | 67674-46-8 |
| 98 | Methyl phenylethyl carbinol | 2344-70-9 |
| 100 | Methyl stearate | 112-61-8 |
| 101 | Methyl nonyl acetaldehyde dimethyl acetal | 68141-17-3 |
| 102 | Methyl nonyl ketone | 112-12-9 |
| 103 | Methyl nonyl acetaldehyde | 110-41-8 |
| 104 | Methyl myristate | 124-10-7 |
| 105 | Methyl linoleate | 112-63-0 |
| 106 | Methyl lavender ketone | 67633-95-8 |
| 108 | Methyl isoeugenol | 93-16-3 |
| 109 | Methyl hexadecanoate | 112-39-0 |
| 110 | Methyl eugenol | 93-15-2 |
| 112 | Methyl epijasmonate | 1211-29-6 |
| 113 | Methyl dihydrojasmonate | 24851-98-7 |
| 114 | Methyl diphenyl ether | 3586-14-9 |
| 117 | Methyl cinnamate | 103-26-4 |
| 119 | Methyl chavicol | 140-67-0 |
| 120 | Methyl beta-naphthyl ketone | 93-08-3 |
| 122 | Methyl 2-octynoate | 111-12-6 |
| 123 | Methyl alpha-cyclogeranate | 28043-10-9 |
| 126 | Methoxycitronellal | 3613-30-7 |
| 128 | Menthone 1,2-glycerol ketal (racemic) | 67785-70-0 |
| 130 | Octahydro-1H-4,7-methanoindene-1-carbaldehyde | 30772-79-3 |
| 134 | 3-(3-(tert-butyl)phenyl)-2-methylpropanal | 62518-65-4 |
| 135 | (E)-4-(4,8-dimethylnona-3,7-dien-1-yl)pyridine | 38462-23-6 |
| 137 | (E)-trideca-3,12-dienenitrile | 134769-33-8 |
| 140 | 2,2-dimethyl-3-(m-tolyl)propan-1-ol | 103694-68-4 |
| 141 | 2,4-dimethyl-4,4a,5,9b-tetrahydroindeno[1,2-d][1,3]dioxine | 27606-09-3 |
| 142 | Maceal | 67845-30-1 |
| 143 | 4-(4-hydroxy-4-methylpentyl)cyclohex-3-ene-1-carbaldehyde | 31906-04-4 |
| 145 | 1-Limonene | 5989-54-8 |
| 146 | (Z)-3-hexen-1-yl-2-cyclopenten-1-one | 53253-09-1 |
| 148 | Linalyl octanoate | 10024-64-3 |
| 149 | Linalyl isobutyrate | 78-35-3 |
| 152 | Linalyl benzoate | 126-64-7 |
| 153 | Linalyl anthranilate | 7149-26-0 |
| 155 | Linalool oxide (furanoid) | 60047-17-8 |
| 156 | linalool oxide | 1365-19-1 |
| 158 | (2Z,6E)-3,7-dimethylnona-2,6-dienenitrile | 61792-11-8 |
| 159 | 3-(4-methylcyclohex-3-en-1-yl)butanal | 6784-13-0 |
| 161 | (2,5-dimethyl-1,3-dihydroinden-2-yl)methanol | 285977-85-7 |
| 162 | 3-(4-(tert-butyl)phenyl)-2-methylpropanal | 80-54-6 |
| 167 | (E)-1-(1-methoxypropoxy)hex-3-ene | 97358-54-8 |
| 168 | Leaf acetal | 88683-94-7 |
| 170 | l-Carveol | 2102-58-1 |
| 174 | Lauryl alcohol | 112-53-8 |
| 175 | Lauryl acetate | 112-66-3 |
| 176 | Lauric acid | 143-07-7 |
| 177 | Lactojasmone | 7011-83-8 |
| 178 | Lauraldehyde | 112-54-9 |
| 179 | 3,6-dimethylhexahydrobenzofuran-2(3H)-one | 92015-65-1 |
| 182 | 4-(1-ethoxyvinyl)-3,3,5,5-tetramethylcyclohexan-1-one | 36306-87-3 |
| 183 | Khusimol | 16223-63-5 |
| 184 | 5-(sec-butyl)-2-(2,4-dimethylcyclohex-3-en-1-yl)-5-methyl-1,3-dioxane | 117933-89-8 |
| 185 | (1-methyl-2-((1,2,2-trimethylbicyclo[3.1.0]hexan-3-yl)methyl)cyclopropyl)methanol | 198404-98-7 |
| 186 | 2-propylheptanenitrile | 208041-98-9 |
| 187 | (E)-6-(pent-3-en-1-yl)tetrahydro-2H-pyran-2-one | 32764-98-0 |
| 189 | 2-hexylcyclopentan-1-one | 13074-65-2 |
| 190 | 2-methyl-4-phenyl-1,3-dioxolane | 33941-99-0 |
| 192 | 2,6,9,10-tetramethyl-1-oxaspiro(4.5)deca-3,6-diene | 71078-31-4 |

TABLE 3-continued

Non-limiting examples of malodor perfume raw materials

| Number | Material Name | CAS Number |
|---|---|---|
| 193 | Isopulegol | 89-79-2 |
| 195 | Isopropyl palmitate | 142-91-6 |
| 196 | Isopropyl myristate | 110-27-0 |
| 197 | Isopropyl dodecanoate | 10233-13-3 |
| 199 | Isopimpinellin | 482-27-9 |
| 206 | Iso3-methylcyclopentadecan-1-one | 3100-36-5 |
| 208 | Isomenthone | 491-07-6 |
| 209 | Isojasmone | 95-41-0 |
| 210 | Isomenthone | 36977-92-1 |
| 211 | Isohexenyl cyclohexenyl carboxaldehyde | 37677-14-8 |
| 212 | Isoeugenyl benzyl ether | 120-11-6 |
| 215 | 1-((2S,3S)-2,3,8,8-tetramethyl-1,2,3,4,5,6,7,8-octahydronaphthalen-2-yl)ethan-1-one | 54464-57-2 |
| 218 | Isocyclocitral | 1335-66-6 |
| 221 | Isobutyl quinoline | 65442-31-1 |
| 227 | Isobornylcyclohexanol | 68877-29-2 |
| 228 | Isobornyl propionate | 2756-56-1 |
| 229 | Isobornyl isobutyrate | 85586-67-0 |
| 230 | Isobornyl cyclohexanol | 66072-32-0 |
| 231 | Isobornyl acetate | 125-12-2 |
| 233 | Isobergamate | 68683-20-5 |
| 234 | Isoamyl undecylenate | 12262-03-2 |
| 238 | Isoamyl laurate | 6309-51-9 |
| 242 | Isoambrettolide | 28645-51-4 |
| 243 | Irisnitrile | 29127-83-1 |
| 244 | Indolene | 68527-79-7 |
| 246 | Indol/Hydroxycitronellal Schiff base | 67801-36-9 |
| 247 | 4,4a,5,9b-tetrahydroindeno[1,2-d][1,3]dioxine | 18096-62-3 |
| 249 | Hydroxy-citronellol | 107-74-4 |
| 252 | 2-cyclododecylpropan-1-ol | 118562-73-5 |
| 253 | Hydrocitronitrile | 54089-83-7 |
| 254 | Hydrocinnamyl alcohol | 122-97-4 |
| 256 | Hydratropaldehyde dimethyl acetal | 90-87-9 |
| 259 | 5-ethyl-4-hydroxy-2-methylfuran-3(2H)-one | 27538-09-6 |
| 260 | 2,3-dihydro-3,3-dimethyl-1H-indene-5-propanal | 173445-44-8 |
| 261 | 3-(3,3-dimethyl-2,3-dihydro-1H-inden-5-yl)propanal | 173445-65-3 |
| 263 | Hexyl octanoate | 1117-55-1 |
| 267 | Hexyl hexanoate | 6378-65-0 |
| 269 | Hexyl cinnamic aldehyde | 101-86-0 |
| 271 | Hexyl benzoate | 6789-88-4 |
| 274 | Hexenyl tiglate | 84060-80-0 |
| 276 | (E)-3,7-dimethylocta-2,6-dien-1-yl palmitate | 3681-73-0 |
| 277 | Hexadecanolide | 109-29-5 |
| 278 | 2-butyl-4,4,6-trimethyl-1,3-dioxane | 54546-26-8 |
| 280 | Ethyl (1R,2R,3R,4R)-3-isopropylbicyclo[2.2.1]hept-5-ene-2-carboxylate | 116126-82-0 |
| 281 | 3a,4,5,6,7,7a-hexahydro-1H-4,7-methanoinden-6-yl acetate | 5413-60-5 |
| 285 | 2-(1-(3,3-dimethylcyclohexyl)ethoxy)-2-methylpropyl propionate | 141773-73-1 |
| 286 | Heliotropine diethyl acetal | 40527-42-2 |
| 288 | Helional | 1205-17-0 |
| 289 | (E)-oxacyclohexadec-13-en-2-one | 111879-80-2 |
| 290 | Gyrane | 24237-00-1 |
| 292 | Guaiol | 489-86-1 |
| 293 | 1-(2,6,6-trimethylcyclohex-2-en-1-yl)pentan-3-one | 68611-23-4 |
| 294 | Ethyl 2-ethyl-6,6-dimethylcyclohex-2-ene-1-carboxylate | 57934-97-1 |
| 295 | Germacrene B | 15423-57-1 |
| 296 | Germacrene D | 23986-74-5 |
| 300 | Geranyl phenylacetate | 102-22-7 |
| 301 | Geranyl phenyl acetate | 71648-43-6 |
| 303 | Geranyl linalool | 1113-21-9 |
| 307 | Geranyl cyclopentanone | 68133-79-9 |
| 316 | gamma-Undecalactone (racemic) | 104-67-6 |
| 317 | gamma-Terpinyl acetate | 10235-63-9 |
| 318 | gamma-Terpineol | 586-81-2 |
| 321 | gamma-Nonalactone | 104-61-0 |
| 322 | gamma-Muurolene | 30021-74-0 |
| 323 | gamma-(E)-6-(pent-3-en-1-yl)tetrahydro-2H-pyran-2-one | 63095-33-0 |
| 324 | gamma-Ionone | 79-76-5 |
| 325 | gamma-Himachalene | 53111-25-4 |
| 328 | gamma-Gurjunene | 22567-17-5 |
| 329 | gamma-Eudesmol | 1209-71-8 |
| 330 | gamma-Dodecalactone | 2305-05-7 |
| 331 | gamma-Damascone | 35087-49-1 |
| 332 | gamma-Decalactone | 706-14-9 |
| 333 | gamma-Cadinene | 39029-41-9 |
| 334 | 1-(3,3-dimethylcyclohexyl)pent-4-en-1-one | 56973-87-6 |
| 335 | 4,6,6,7,8,8-hexamethyl-1,3,4,6,7,8-hexahydrocyclopenta[g]isochromene | 1222-05-5 |
| 336 | Furfuryl octanoate | 39252-03-4 |
| 338 | Furfuryl hexanoate | 39252-02-3 |
| 339 | Furfuryl heptanoate | 39481-28-2 |
| 342 | 2-methyldecanenitrile | 69300-15-8 |
| 343 | 8,8-dimethyl-3a,4,5,6,7,7a-hexahydro-1H-4,7-methanoinden-6-yl propionate | 76842-49-4 |
| 344 | Ethyl (3aR,4S,7R,7aR)-octahydro-3aH-4,7-methanoindene-3a-carboxylate | 80657-64-3 |
| 347 | Diethyl cyclohexane-1,4-dicarboxylate | 72903-27-6 |
| 349 | (6-isopropyl-9-methyl-1,4-dioxaspiro[4.5]decan-2-yl)methanol | 63187-91-7 |
| 350 | 2-isobutyl-4-methyltetrahydro-2H-pyran-4-ol | 63500-71-0 |
| 352 | Undec-10-enenitrile | 53179-04-7 |
| 353 | (Z)-6-ethylideneoctahydro-2H-5,8-methanochromen-2-one | 69486-14-2 |
| 356 | 3-(2-ethylphenyl)-2,2-dimethylpropanal | 67634-15-5 |
| 358 | (E)-4,8-dimethyldeca-4,9-dienal | 71077-31-1 |
| 359 | (E)-4-((3aR,4R,7R,7aR)-1,3a,4,6,7,7a-hexahydro-5H-4,7-methanoinden-5-ylidene)-3-methylbutan-2-ol | 501929-47-1 |
| 360 | 8,8-dimethyl-3a,4,5,6,7,7a-hexahydro-1H-4,7-methanoinden-6-yl acetate | 171102-41-3 |
| 361 | 3-(4-ethylphenyl)-2,2-dimethylpropanenitrile | 134123-93-6 |
| 362 | 2-heptylcyclopentan-1-one | 137-03-1 |
| 363 | 1-ethoxyethoxy Cyclododecane | 389083-83-4 |
| 364 | 3-cyclohexene-1-carboxylic acid, 2,6,6-trimethyl-, methyl ester | 815580-59-7 |
| 368 | Farnesyl acetate | 29548-30-9 |
| 369 | Farnesol | 4602-84-0 |
| 370 | Oxacyclohexadecan-2-one | 106-02-5 |
| 371 | 1-cyclopentadec-4-en-1-one | 14595-54-1 |
| 372 | 1-cyclopentadec-4-en-1-one | 35720-57-1 |
| 373 | 2-methoxy-4-(4-methylenetetrahydro-2H-pyran-2-yl)phenol | 128489-04-3 |
| 374 | Eugenyl acetate | 93-28-7 |
| 375 | Eugenol | 97-53-0 |
| 377 | Ethylmethylphenylglycidate | 77-83-8 |
| 378 | Ethylene brassylate | 105-95-3 |
| 381 | Ethyl undecylenate | 692-86-4 |
| 385 | Ethyl palmitate | 628-97-7 |
| 386 | Ethyl nonanoate | 123-29-5 |
| 388 | Ethyl myristate | 124-06-1 |
| 390 | Ethyl linalool | 10339-55-6 |
| 391 | Ethyl laurate | 106-33-2 |
| 394 | Ethyl hexyl ketone | 925-78-0 |
| 397 | Ethyl decanoate | 110-38-3 |
| 398 | Ethyl gamma-Safranate | 35044-57-6 |
| 407 | Ethyl 3-phenylglycidate | 121-39-1 |
| 413 | 6-ethyl-2,10,10-trimethyl-1-oxaspiro[4.5]deca-3,6-diene | 79893-63-3 |
| 414 | Elemol | 639-99-6 |
| 415 | (2-(1-ethoxyethoxy)ethyl)benzene | 2556-10-7 |
| 416 | (E)-3-methyl-5-(2,2,3-trimethylcyclopent-3-en-1-yl)pent-4-en-2-ol | 67801-20-1 |
| 417 | d-xylose | 58-86-6 |
| 418 | (E)-4-((3aS,7aS)-octahydro-5H-4,7-methanoinden-5-ylidene)butanal | 30168-23-1 |
| 421 | Dodecanal dimethyl acetal | 14620-52-1 |

TABLE 3-continued

Non-limiting examples of malodor perfume raw materials

| Number | Material Name | CAS Number |
|---|---|---|
| 424 | d-Limonene | 5989-27-5 |
| 425 | Dipropylene Glycol | 25265-71-8 |
| 426 | Dispirone | 83863-64-3 |
| 428 | Diphenyloxide | 101-84-8 |
| 429 | Diphenylmethane | 101-81-5 |
| 432 | Dimethyl benzyl carbinyl butyrate | 10094-34-5 |
| 436 | 2,6-dimethyloct-7-en-4-one | 1879-00-1 |
| 441 | Octahydro-1H-4,7-methanoinden-5-yl acetate | 64001-15-6 |
| 444 | Dihydrocarveol acetate | 20777-49-5 |
| 445 | Dihydrocarveol | 619-01-2 |
| 449 | Dihydro Linalool | 18479-51-1 |
| 450 | Dihydro Isojasmonate | 37172-53-5 |
| 453 | Dibutyl sulfide | 544-40-1 |
| 457 | Dibenzyl | 103-29-7 |
| 459 | delta-Undecalactone | 710-04-3 |
| 461 | delta-Elemene | 20307-84-0 |
| 462 | delta-Guaiene | 3691-11-0 |
| 463 | delta-Dodecalactone | 713-95-1 |
| 464 | delta-Decalactone | 705-86-2 |
| 465 | delta-Cadinene | 483-76-1 |
| 466 | delta-damascone | 57378-68-4 |
| 467 | delta-Amorphene | 189165-79-5 |
| 468 | delta-3-Carene | 13466-78-9 |
| 470 | Decylenic alcohol | 13019-22-2 |
| 471 | Decyl propionate | 5454-19-3 |
| 473 | Decanal diethyl acetal | 34764-02-8 |
| 474 | Decahydro-beta-naphthol | 825-51-4 |
| 475 | 1-cyclohexylethyl (E)-but-2-enoate | 68039-69-0 |
| 478 | 3-(4-isopropylphenyl)-2-methylpropanal | 103-95-7 |
| 479 | Cyclotetradecane | 295-17-0 |
| 480 | Cyclopentadecanone | 502-72-7 |
| 482 | Cyclohexyl salicylate | 25485-88-5 |
| 484 | 3a,4,5,6,7,7a-hexahydro-1H-4,7-methanoinden-6-yl butyrate | 113889-23-9 |
| 485 | Cyclic ethylene dodecanedioate | 54982-83-1 |
| 486 | 8,8-dimethyl-1,2,3,4,5,6,7,8-octahydronaphthalene-2-carbaldehyde | 68991-97-9 |
| 487 | 3a,4,5,6,7,7a-hexahydro-1H-4,7-methanoinden-5-yl isobutyrate | 67634-20-2 |
| 488 | Curzerene | 17910-09-7 |
| 491 | Cumic alcohol | 536-60-7 |
| 493 | Coumarone | 1646-26-0 |
| 497 | 2-(3-phenylpropyl)pyridine | 2110-18-1 |
| 498 | Dodecanenitrile | 2437-25-4 |
| 501 | (E)-cycloheptadec-9-en-1-one | 542-46-1 |
| 502 | Citryl acetate | 6819-19-8 |
| 503 | Citrus Propanol | 15760-18-6 |
| 505 | Citronitrile | 93893-89-1 |
| 519 | Citral propylene glycol acetal | 10444-50-5 |
| 520 | Citral dimethyl acetal | 7549-37-3 |
| 521 | Citral diethyl acetal | 7492-66-2 |
| 524 | cis-Ocimene | 3338-55-4 |
| 527 | cis-Limonene oxide | 13837-75-7 |
| 529 | Cis-iso-ambrettolide | 36508-31-3 |
| 530 | cis-6-nonenol | 35854-86-5 |
| 531 | cis-carveol | 1197-06-4 |
| 532 | cis-4-Decen-1-al | 21662-09-9 |
| 534 | cis-3-hexenyl-cis-3-hexenoate | 61444-38-0 |
| 537 | cis-3-Hexenyl salicylate | 65405-77-8 |
| 541 | Cis-3-hexenyl Benzoate | 25152-85-6 |
| 544 | cis-3-Hexenyl 2-methylbutyrate | 53398-85-9 |
| 546 | cis-3, cis-6-nonadienol | 53046-97-2 |
| 548 | Cinnamyl propionate | 103-56-0 |
| 550 | Cinnamyl isobutyrate | 103-59-3 |
| 551 | Cinnamyl formate | 104-65-4 |
| 552 | Cinnamyl cinnamate | 122-69-0 |
| 553 | Cinnamyl acetate | 103-54-8 |
| 555 | Cinnamic alcohol | 104-54-1 |
| 558 | Cetyl alcohol | 36653-82-4 |
| 559 | (E)-1-(2,6,6-trimethylcyclohex-2-en-1-yl)hepta-1,6-dien-3-one | 79-78-7 |
| 560 | 2-methyl-4-(2,6,6-trimethylcyclohex-1-en-1-yl)butanal | 65405-84-7 |
| 561 | (3aR,5aR,9aR,9bR)-3a,6,6,9a-tetramethyldodecahydronaphtho[2,1-b]furan | 3738-00-9 |
| 562 | 1,6-dioxacycloheptadecan-7-one | 6707-60-4 |
| 563 | 1-(6-(tert-butyl)-1,1-dimethyl-2,3-dihydro-1H-inden-4-yl)ethan-1-one | 13171-00-1 |
| 565 | Cedryl methyl ether | 19870-74-7 |
| 566 | Cedryl formate | 39900-38-4 |
| 567 | Cedryl acetate | 77-54-3 |
| 568 | (4Z,8Z)-1,5,9-trimethyl-13-oxabicyclo[10.1.0]trideca-4,8-diene | 71735-79-0 |
| 569 | Cedrol | 77-53-2 |
| 570 | 5-methyl-1-(2,2,3-trimethylcyclopent-3-en-1-yl)-6-oxabicyclo[3.2.1]octane | 139539-66-5 |
| 571 | 5-methyl-1-(2,2,3-trimethylcyclopent-3-en-1-yl)-6-oxabicyclo[3.2.1]octane | 426218-78-2 |
| 572 | 1,1,2,3,3-pentamethyl-1,2,3,5,6,7-hexahydro-4H-inden-4-one | 33704-61-9 |
| 573 | Caryophyllene alcohol acetate | 32214-91-8 |
| 574 | Caryolan-1-ol | 472-97-9 |
| 577 | Carvyl acetate | 97-42-7 |
| 578 | Caprylnitrile | 124-12-9 |
| 580 | Caprylic alcohol | 111-87-5 |
| 581 | Caprylic acid | 124-07-2 |
| 582 | Capric acid | 334-48-5 |
| 584 | Capraldehyde | 112-31-2 |
| 586 | 3-(4-methoxyphenyl)-2-methylpropanal | 5462-06-6 |
| 587 | Camphorquinone | 10373-78-1 |
| 589 | Camphene | 79-92-5 |
| 591 | Ethyl 2-methyl-4-oxo-6-pentylcyclohex-2-ene-1-carboxylate | 59151-19-8 |
| 592 | Butylated hydroxytoluene | 128-37-0 |
| 594 | Butyl stearate | 123-95-5 |
| 595 | Butyl butyryl lactate | 7492-70-8 |
| 599 | Butyl 10-undecenoate | 109-42-2 |
| 600 | 2-methyl-4-(2,2,3-trimethylcyclopent-3-en-1-yl)butan-1-ol | 72089-08-8 |
| 601 | 3-(4-(tert-butyl)phenyl)propanal | 18127-01-0 |
| 603 | Bornyl isobutyrate | 24717-86-0 |
| 604 | Bornyl acetate | 76-49-3 |
| 606 | 2-ethoxy-2,6,6-trimethyl-9-methylenebicyclo[3.3.1]nonane | 68845-00-1 |
| 607 | (ethoxymethoxy)cyclododecane | 58567-11-6 |
| 608 | Bisabolene | 495-62-5 |
| 609 | Bigarade oxide | 72429-08-4 |
| 610 | beta-Vetivone | 18444-79-6 |
| 611 | beta-Terpinyl acetate | 10198-23-9 |
| 612 | beta-Terpineol | 138-87-4 |
| 613 | beta-Sinensal | 60066-88-8 |
| 614 | beta-Sesquiphellandrene | 20307-83-9 |
| 615 | beta-Selinene | 17066-67-0 |
| 616 | beta-Santalol | 77-42-9 |
| 618 | beta-Pinene | 127-91-3 |
| 620 | beta-Naphthyl ethyl ether | 93-18-5 |
| 621 | beta-Patchoulline | 514-51-2 |
| 624 | beta-Himachalene Oxide | 57819-73-5 |
| 625 | beta-Himachalene | 1461-03-6 |
| 626 | beta-Guaiene | 88-84-6 |
| 627 | (2,2-dimethoxyethyl)benzene | 101-48-4 |
| 628 | beta-Farnesene | 18794-84-8 |
| 631 | beta-Copaene | 18252-44-3 |
| 632 | beta-Cedrene | 546-28-1 |
| 633 | beta-Caryophyllene | 87-44-5 |
| 635 | beta-Bisabolol | 15352-77-9 |
| 636 | Beta ionone epoxide | 23267-57-4 |
| 638 | Bergaptene | 484-20-8 |
| 639 | Benzyl-tert-butanol | 103-05-9 |
| 644 | Benzyl laurate | 140-25-0 |
| 649 | Benzyl dimethyl carbinol | 100-86-7 |
| 650 | Benzyl cinnamate | 103-41-3 |
| 653 | Benzyl benzoate | 120-51-4 |
| 655 | Benzophenone | 119-61-9 |
| 658 | 7-isopentyl-2H-benzo[b][1,4]dioxepin-3(4H)-one | 362467-67-2 |

TABLE 3-continued

Non-limiting examples of malodor perfume raw materials

| Number | Material Name | CAS Number |
|---|---|---|
| 659 | 2'-isopropyl-1,7,7-trimethylspiro[bicyclo[2.2.1]heptane-2,4'-[1,3]dioxane] | 188199-50-0 |
| 660 | 4-(4-methylpent-3-en-1-yl)cyclohex-3-ene-1-carbonitrile | 21690-43-7 |
| 661 | Aurantiol | 89-43-0 |
| 663 | Anisyl phenylacetate | 102-17-0 |
| 668 | Methyl (E)-octa-4,7-dienoate | 189440-77-5 |
| 671 | Amyl Cinnamate | 3487-99-8 |
| 673 | (3aR,5aS,9aS,9bR)-3a,6,6,9a-tetramethyldodecahydronaphtho[2,1-b]furan | 6790-58-5 |
| 674 | (4aR,5R,7aS,9R)-2,2,5,8,9,9a-hexamethyloctahydro-4H-4a,9-methanoazuleno[5,6-d][1,3]dioxole | 211299-54-6 |
| 675 | 2,5,5-trimethyl-1,2,3,4,5,6,7,8-octahydronaphthalen-2-ol | 71832-76-3 |
| 676 | 2,5,5-trimethyl-1,2,3,4,5,6,7,8-octahydronaphthalen-2-ol | 41199-19-3 |
| 677 | 1-((2-(tert-butyl)cyclohexyl)oxy)butan-2-ol | 139504-68-0 |
| 678 | (3S,5aR,7aS,11aS,11bR)-3,8,8,11a-tetramethyldodecahydro-5H-3,5a-epoxynaphtho[2,1-c]oxepine | 57345-19-4 |
| 679 | 2,2,6,6,7,8,8-heptamethyldecahydro-2H-indeno[4,5-b]furan | 476332-65-7 |
| 680 | 2,2,6,6,7,8,8-heptamethyldecahydro-2H-indeno[4,5-b]furan | 647828-16-8 |
| 681 | Amber acetate | 37172-02-4 |
| 682 | Alpinofix ® | 811436-82-5 |
| 683 | alpha-Thujone | 546-80-5 |
| 684 | alpha-Vetivone | 15764-04-2 |
| 686 | alpha-Terpinyl propionate | 80-27-3 |
| 691 | alpha-Sinensal | 17909-77-2 |
| 692 | alpha-Selinene | 473-13-2 |
| 693 | alpha-Santalene | 512-61-8 |
| 694 | alpha-Santalol | 115-71-9 |
| 696 | alpha-Patchoulene | 560-32-7 |
| 697 | alpha-neobutenone | 56973-85-4 |
| 698 | alpha-Muurolene | 10208-80-7 |
| 700 | alpha-methyl ionone | 127-42-4 |
| 702 | alpha-Limonene | 138-86-3 |
| 704 | alpha-Irone | 79-69-6 |
| 706 | alpha-Humulene | 6753-98-6 |
| 707 | alpha-Himachalene | 186538-22-7 |
| 708 | alpha-Gurjunene | 489-40-7 |
| 709 | alpha-Guaiene | 3691-12-1 |
| 710 | alpha-Farnesene | 502-61-4 |
| 711 | alpha-Fenchene | 471-84-1 |
| 712 | alpha-Eudesmol | 473-16-5 |
| 713 | alpha-Curcumene | 4176-17-4 |
| 714 | alpha-Cubebene | 17699-14-8 |
| 715 | alpha-Cedrene epoxide | 13567-39-0 |
| 716 | alpha-Cadinol | 481-34-5 |
| 717 | alpha-Cadinene | 24406-05-1 |
| 718 | alpha-Bisabolol | 515-69-5 |
| 719 | alpha-bisabolene | 17627-44-0 |
| 720 | alpha-Bergamotene | 17699-05-7 |
| 721 | alpha-Amylcinnamyl alcohol | 101-85-9 |
| 722 | alpha-Amylcinnamyl acetate | 7493-78-9 |
| 723 | alpha-Amylcinnamaldehyde diethyl acetal | 60763-41-9 |
| 724 | alpha-Amylcinnamaldehyde | 122-40-7 |
| 725 | alpha-Amorphene | 23515-88-0 |
| 726 | alpha-Agarofuran | 5956-12-7 |
| 727 | 1-methyl-4-(4-methyl-3-penten-1-yl)-3-Cyclohexene-1-carboxaldehyde | 52475-86-2 |
| 730 | 1-Phenyl-2-pentanol | 705-73-7 |
| 731 | 1-Phenyl-3-methyl-3-pentanol | 10415-87-9 |
| 733 | 2,3,4-trimethoxy-benzaldehyde | 2103-57-3 |
| 735 | 2,4,5-trimethoxy-benzaldehyde | 4460-86-0 |
| 736 | 2,4,6-trimethoxybenzaldehyde | 830-79-5 |
| 738 | 2,4-Nonadienal | 6750-03-4 |
| 741 | 2,6,10-Trimethylundecanal | 105-88-4 |
| 742 | alpha,4-Dimethyl benzenepropanal | 41496-43-9 |
| 746 | Allyl cyclohexyl propionate | 2705-87-5 |
| 748 | Allyl amyl glycolate | 67634-00-8 |
| 750 | Allo-aromadendrene | 25246-27-9 |
| 752 | Aldehyde C-11 | 143-14-6 |
| 754 | Methyl (E)-2-(((3,5-dimethylcyclohex-3-en-1-yl)methylene)amino)benzoate | 94022-83-0 |
| 757 | 2,6,10-trimethylundec-9-enal | 141-13-9 |
| 758 | Acetoxymethyl-isolongifolene (isomers) | 59056-62-1 |
| 763 | Acetate C9 | 143-13-5 |
| 764 | Acetarolle ® | 744266-61-3 |
| 766 | Acetaldehyde phenylethyl propyl acetal | 7493-57-4 |
| 767 | Acetaldehyde dipropyl acetal | 105-82-8 |
| 768 | Acetaldehyde benzyl 2-methoxyethyl acetal | 7492-39-9 |
| 769 | (Z)-2-(4-methylbenzylidene)heptanal | 84697-09-6 |
| 770 | 9-decenal | 39770-05-3 |
| 771 | 8-Hexadecenolide | 123-69-3 |
| 772 | 7-Methoxycoumarin | 531-59-9 |
| 774 | 7-epi-alpha-Selinene | 123123-37-5 |
| 775 | 7-eip-alpha-Eudesmol | 123123-38-6 |
| 776 | 7-Acetyl-1,1,3,4,4,6-hexamethyltetralin | 1506-02-1 |
| 778 | 6-Isopropylquinoline | 135-79-5 |
| 781 | 6,6-dimethyl-2-norpinene-2-propionaldehyde | 33885-51-7 |
| 782 | 6,10,14-trimethyl-2-Pentadecanone | 502-69-2 |
| 786 | 5-Isopropenyl-2-methyl-2-vinyltetrahydrofuran | 13679-86-2 |
| 788 | 5-Cyclohexadecenone | 37609-25-9 |
| 791 | 4-Terpinenol | 562-74-3 |
| 792 | 4-Pentenophenone | 3240-29-7 |
| 800 | 4-Carvomenthenol | 28219-82-1 |
| 802 | 4,5,6,7-Tetrahydro-3,6-dimethylbenzofuran | 494-90-6 |
| 803 | 4-(p-Methoxyphenyl)-2-butanone | 104-20-1 |
| 804 | 3-Thujopsanone | 25966-79-4 |
| 805 | 3-Propylidenephthalide | 17369-59-4 |
| 806 | 3-Nonylacrolein | 20407-84-5 |
| 807 | 3-Methyl-5-phenyl-1-pentanal | 55066-49-4 |
| 814 | 3-Hexenyl isovalerate | 10032-11-8 |
| 821 | 3,6-Dimethyl-3-octanyl acetate | 60763-42-0 |
| 824 | 3,4,5-trimethoxybenzaldehyde | 86-81-7 |
| 826 | 3-(p-Isopropylphenyl)propionaldehyde | 7775-00-0 |
| 827 | 2-Undecenenitrile | 22629-48-7 |
| 828 | 2-Undecenal | 2463-77-6 |
| 829 | 2-trans-6-trans-Nonadienal | 17587-33-6 |
| 831 | 2-Phenylethyl butyrate | 103-52-6 |
| 833 | 2-Phenyl-3-(2-furyl)prop-2-enal | 57568-60-2 |
| 834 | 2-Phenoxyethanol | 122-99-6 |
| 837 | 2-Nonen-1-al | 2463-53-8 |
| 839 | 2-Nonanol | 628-99-9 |
| 840 | 2-Nonanone | 821-55-6 |
| 849 | 2-Isobutyl quinoline | 93-19-6 |
| 850 | 2-Hexylidene cyclopentanone | 17373-89-6 |
| 852 | 2-Heptyl tetrahydrofuran | 2435-16-7 |
| 856 | 2-Decenal | 3913-71-1 |
| 864 | 2,6-Nonadienal | 26370-28-5 |
| 865 | 2,6-Nonadien-1-ol | 7786-44-9 |
| 866 | 2,6-dimethyl-octanal | 7779-07-9 |
| 868 | 1-Decanol | 112-30-1 |
| 869 | 1-Hepten-1-ol, 1-acetate | 35468-97-4 |
| 870 | 10-Undecen-1-ol | 112-43-6 |
| 871 | 10-Undecenal | 112-45-8 |
| 872 | 10-epi-gamma-Eudesmol | 15051-81-7 |
| 873 | 1,8-Thiocineol | 68391-28-6 |
| 876 | 1,3,5-undecatriene | 16356-11-9 |
| 877 | 1,2-Dihydrolinalool | 2270-57-7 |
| 878 | 1,3,3-trimethyl-2-norbornanyl acetate | 13851-11-1 |
| 879 | 1,1,2,3,3-Pentamethylindan | 1203-17-4 |
| 881 | (Z)-6,10-dimethylundeca-5,9-dien-2-yl acetate | 3239-37-0 |
| 884 | (Z)-3-Dodecenal | 68141-15-1 |
| 885 | (S)-gamma-Undecalactone | 74568-05-1 |
| 886 | (R)-gamma-Undecalactone | 74568-06-2 |
| 890 | (E)-6,10-dimethylundeca-5,9-dien-2-yl acetate | 3239-35-8 |

TABLE 3-continued

Non-limiting examples of malodor perfume raw materials

| Number | Material Name | CAS Number |
|---|---|---|
| 892 | (2Z)-3-methyl-5-phenyl-2-Pentenenitrile | 53243-59-7 |
| 893 | (2S,5S,6S)-2,6,10,10-tetramethyl-1-oxaspiro[4_5]decan-6-ol | 65620-50-0 |
| 894 | (2E)-3-methyl-5-phenyl-2-pentenenitrile | 53243-60-0 |
| 897 | (+)-Dihydrocarveol | 22567-21-1 |
| 905 | Menthone | 89-80-5 |
| 908 | (R,E)-2-methyl-4-(2,2,3-trimethylcyclopent-3-en-1-yl)but-2-en-1-ol | 185068-69-3 |
| 912 | 2-(8-isopropyl-6-methylbicyclo[2.2.2]oct-5-en-2-yl)-1,3-dioxolane | 68901-32-6 |
| 913 | gamma-methyl ionone | 7388-22-9 |
| 914 | 3-(3-isopropylphenyl)butanal | 125109-85-5 |
| 916 | 3-(1-ethoxyethoxy)-3,7-dimethylocta-1,6-diene | 40910-49-4 |
| 919 | 3a,4,5,6,7,7a-hexahydro-1H-4,7-methanoinden-6-yl propionate | 17511-60-3 |
| 920 | Bulnesol | 22451-73-6 |
| 922 | Benzyl phenylacetate | 102-16-9 |
| 923 | Benzoin | 119-53-9 |
| 924 | (E)-1,2,4-trimethoxy-5-(prop-1-en-1-yl)benzene | 2883-98-9 |
| 925 | alpha,alpha,6,6-tetramethyl bicyclo[3.1.1]hept-2-ene-propanal | 33885-52-8 |
| 926 | 7-epi-sesquithujene | 159407-35-9 |
| 927 | 5-Acetyl-1,1,2,3,3,6-hexamethylindan | 15323-35-0 |
| 928 | 3-Methylphenethyl alcohol | 1875-89-4 |
| 929 | 3,6-Nonadien-1-ol | 76649-25-7 |
| 930 | 2-Tridecenal | 7774-82-5 |
| 933 | Patchouli alcohol | 5986-55-0 |
| 937 | p-Cresyl isobutyrate | 103-93-5 |
| 939 | p-Cresyl n-hexanoate | 68141-11-7 |
| 941 | 5-hexyl-4-methyldihydrofuran-2(3H)-one | 67663-01-8 |
| 942 | Ethyl (2Z,4E)-deca-2,4-dienoate | 3025-30-7 |
| 943 | Pelargene | 68039-40-7 |
| 945 | 2-cyclohexylidene-2-phenylacetonitrile | 10461-98-0 |
| 946 | Perillaldehyde | 2111-75-3 |
| 947 | Perillyl acetate | 15111-96-3 |
| 948 | Perillyl alcohol | 536-59-4 |
| 950 | (2-isopropoxyethyl)benzene | 68039-47-4 |
| 951 | Ethyl (2Z,4E)-deca-2,4-dienoate | 313973-37-4 |
| 953 | (2-(cyclohexyloxy)ethyl)benzene | 80858-47-5 |
| 954 | Phenethyl 2-methylbutyrate | 24817-51-4 |
| 955 | Phenethyl alcohol | 60-12-8 |
| 959 | Phenethyl phenylacetate | 102-20-5 |
| 962 | Phenoxanol | 55066-48-3 |
| 965 | Phenyl benzoate | 93-99-2 |
| 967 | Phenyl ethyl benzoate | 94-47-3 |
| 969 | Phenylacetaldehyde ethyleneglycol acetal | 101-49-5 |
| 973 | 2-(6,6-dimethylbicyclo[3.1.1]hept-2-en-2-yl)acetaldehyde | 30897-75-7 |
| 974 | Pinocarveol | 5947-36-4 |
| 976 | Piperonyl acetone | 55418-52-5 |
| 978 | 3a,4,5,6,7,7a-hexahydro-1H-4,7-methanoinden-6-yl pivalate | 68039-44-1 |
| 980 | (4aR,8aS)-7-methyloctahydro-1,4-methanonaphthalen-6(2H)-one | 41724-19-0 |
| 982 | p-Menth-3-en-1-ol | 586-82-3 |
| 985 | (E)-3,3-dimethyl-5-(2,2,3-trimethylcyclopent-3-en-1-yl)pent-4-en-2-ol | 107898-54-4 |
| 988 | 1-methyl-4-(4-methylpent-3-en-1-yl)cyclohex-3-ene-1-carbaldehyde | 52474-60-9 |
| 993 | Propylene glycol | 57-55-6 |
| 998 | p-Tolyl phenylacetate | 101-94-0 |
| 1000 | Ethyl 2,4,7-decatrienoate | 78417-28-4 |
| 1003 | 2-benzyl-4,4,6-trimethyl-1,3-dioxane | 67633-94-7 |
| 1006 | 2,4-dimethyl-4-phenyltetrahydrofuran | 82461-14-1 |
| 1007 | (2R,4a'R,8a'R)-3',7'-dimethyl-3',4',4a',5',8',8a'-hexahydro-1'H-spiro[oxirane-2,2'-[1,4]methanonaphthalene] | 41816-03-9 |
| 1008 | (Z)-6-ethylideneoctahydro-2H-5,8-methanochromene | 93939-86-7 |
| 1009 | 2-((S)-1-((S)-3,3-dimethylcyclohexyl)ethoxy)-2-oxoethyl propionate | 236391-76-7 |
| 1010 | Methyl 2,2-dimethyl-6-methylenecyclohexane-1-carboxylate | 81752-87-6 |
| 1012 | 2-methyl-5-phenylpentan-1-ol | 25634-93-9 |
| 1016 | 4-methyl-2-phenyl-3,6-dihydro-2H-pyran | 60335-71-9 |
| 1020 | Sabinol | 471-16-9 |
| 1021 | Safrole | 94-59-7 |
| 1022 | 2,2,7,9-tetramethylspiro(5.5)undec-8-en-1-one | 502847-01-0 |
| 1023 | 3-methyl-5-(2,2,3-trimethylcyclopent-3-en-1-yl)pentan-2-ol | 65113-99-7 |
| 1024 | (Z)-2-ethyl-4-(2,2,3-trimethylcyclopent-3-en-1-yl)but-2-en-1-ol | 28219-61-6 |
| 1025 | (E)-2-methyl-4-(2,2,3-trimethylcyclopent-3-en-1-yl)but-2-en-1-ol | 28219-60-5 |
| 1026 | 5-methoxyoctahydro-1H-4,7-methanoindene-2-carbaldehyde | 86803-90-9 |
| 1027 | 5-methoxyoctahydro-1H-4,7-methanoindene-2-carbaldehyde | 193425-86-4 |
| 1028 | Sclareol | 515-03-7 |
| 1029 | Sclareol oxide | 5153-92-4 |
| 1031 | Selina-3,7(11)-diene | 6813-21-4 |
| 1032 | 2-(1-(3,3-dimethylcyclohexyl)ethoxy)-2-methylpropyl cyclopropanecarboxylate | 477218-42-1 |
| 1033 | 3-(4-isobutylphenyl)-2-methylpropanal | 6658-48-6 |
| 1035 | Spathulenol | 6750-60-3 |
| 1036 | Spirambrene | 533925-08-5 |
| 1037 | Spirodecane | 6413-26-9 |
| 1038 | 1-(spiro[4.5]dec-7-en-7-yl)pent-4-en-1-one | 224031-70-3 |
| 1042 | 2-(4-methylthiazol-5-yl)ethan-1-ol | 137-00-8 |
| 1043 | 2-(heptan-3-yl)-1,3-dioxolane | 4359-47-1 |
| 1045 | (Z)-dodec-4-enal | 21944-98-9 |
| 1046 | tau-Cadinol | 5937-11-1 |
| 1047 | tau-Muurolol | 19912-62-0 |
| 1053 | Tetrahydrojasmone | 13074-63-0 |
| 1057 | 2,6,10,10-tetramethyl-1-oxaspiro[4.5]dec-6-ene | 36431-72-8 |
| 1059 | Thiomenthone | 38462-22-5 |
| 1060 | Thujopsene | 470-40-6 |
| 1062 | Thymol methyl ether | 1076-56-8 |
| 1063 | 1-(2,2,6-trimethylcyclohexyl)hexan-3-ol | 70788-30-6 |
| 1064 | trans,trans-2,4-Nonadienal | 5910-87-2 |
| 1065 | trans,trans-Farnesol | 106-28-5 |
| 1066 | trans-2,cis-6-Nonadienal | 557-48-2 |
| 1067 | trans-2-Decenal | 3913-81-3 |
| 1070 | trans-2-Nonen-1-al | 18829-56-6 |
| 1072 | trans-3, cis-6-nonadienol | 56805-23-3 |
| 1073 | trans-4-Decen-1-al | 65405-70-1 |
| 1075 | trans-ambrettolide | 51155-12-5 |
| 1077 | trans-beta-ocimene | 13877-91-3 |
| 1078 | trans-beta-Ocimene | 3779-61-1 |
| 1082 | trans-Geraniol | 106-24-1 |
| 1083 | trans-Hedione | 2570-03-8 |
| 1085 | 7-(1,1-Dimethylethyl)-2H-1,5-benzodioxepin-3(4H)-one | 195251-91-3 |
| 1089 | Tricyclone | 68433-81-8 |
| 1090 | Tridecyl alcohol | 112-70-9 |
| 1091 | Triethyl citrate | 77-93-0 |
| 1093 | Methyl 2-((1-hydroxy-3-phenylbutyl)amino)benzoate | 144761-91-1 |
| 1095 | 1-((2E,5Z,9Z)-2,6,10-trimethylcyclododeca-2,5,9-trien-1-yl)ethan-1-one | 28371-99-5 |
| 1097 | Decahydro-2,6,6,7,8,8-hexamethyl-2h-indeno(4,5-b)furan | 338735-71-0 |
| 1099 | 13-methyl oxacyclopentadec-10-en-2-one | 365411-50-3 |
| 1102 | Undecanal | 112-44-7 |
| 1104 | (E)-4-methyldec-3-en-5-ol | 81782-77-6 |
| 1105 | Valencene | 4630-07-3 |
| 1107 | Valerianol | 20489-45-6 |
| 1111 | Vanillin isobutyrate | 20665-85-4 |
| 1113 | Vaniwhite ® | 5533-03-9 |

TABLE 3-continued

Non-limiting examples of malodor perfume raw materials

| Number | Material Name | CAS Number |
|---|---|---|
| 1116 | (Z)-2-methyl-4-(2,6,6-trimethylcyclohex-2-en-1-yl)but-2-enal | 68555-62-4 |
| 1117 | Methyl 2,4-dihydroxy-3,6-dimethylbenzoate | 4707-47-5 |
| 1120 | 1-methoxy-3a,4,5,6,7,7a-hexahydro-1H-4,7-methanoindene | 27135-90-6 |
| 1121 | Methyl (Z)-2-((3-(4-(tert-butyl)phenyl)-2-methylpropylidene)amino)benzoate | 91-51-0 |
| 1125 | (Z)-hex-3-en-1-yl isobutyrate | 41519-23-7 |
| 1126 | Vertacetal | 5182-36-5 |
| 1129 | 1-((3R,3aR,7R,8aS)-3,6,8,8-tetramethyl-2,3,4,7,8,8a-hexahydro-1H-3a,7-methanoazulen-5-yl)ethan-1-one | 32388-55-9 |
| 1131 | Methyl (Z)-2-(((2,4-dimethylcyclohex-3-en-1-yl)methylene)amino)benzoate | 68738-99-8 |
| 1135 | Vetiverol | 89-88-3 |
| 1136 | Vetivert Acetate | 117-98-6 |
| 1137 | Decahydro-3H-spiro[furan-2,5'-[4,7]methanoindene] | 68480-11-5 |
| 1138 | (2Z,6E)-nona-2,6-dienenitrile | 67019-89-0 |
| 1139 | (Z)-cyclooct-4-en-1-yl methyl carbonate | 87731-18-8 |
| 1140 | (1aR,4S,4aS,7R,7aS,7bS)-1,1,4,7-tetramethyldecahydro-1H-cyclopropa[e]azulen-4-ol | 552-02-3 |
| 1142 | 3,5,5,6,7,8,8-heptamethyl-5,6,7,8-tetrahydronaphthalene-2-carbonitrile | 127459-79-4 |
| 1143 | (1S,2S,3S,5R)-2,6,6-trimethylspiro[bicyclo[3.1.1]heptane-3,1'-cyclohexan]-2'-en-4'-one | 133636-82-5 |
| 1144 | 1',1',5',5'-tetramethylhexahydro-2'H,5'H-spiro[[1,3]dioxolane-2,8'-[2,4a]methanonaphthalene] | 154171-76-3 |
| 1145 | 1',1',5',5'-tetramethylhexahydro-2'H,5'H-spiro[[1,3]dioxolane-2,8'-[2,4a]methanonaphthalene] K | 154171-77-4 |
| 1146 | 4-(4-hydroxy-3-methoxyphenyl)butan-2-one | 122-48-5 |
| 1147 | (1R,8aR)-4-isopropyl-1,6-dimethyl-1,2,3,7,8,8a-hexahydronaphthalene | 41929-05-9 |
| 1148 | 4,5-epoxy-4,11,11-trimethyl-8-methylenebicyclo(7.2.0)undecane | 1139-30-6 |
| 1149 | 1,3,4,6,7,8alpha-hexahydro-1,1,5,5-tetramethyl-2H-2,4alpha-methanophtalen-8(5H)-one | 23787-90-8 |

Without being bound by theory, solvents are used in cosmetic and topical medicinal preparations where good absorption through the skin is desired, therefore, changing the rheology properties of these solvents improves retention in the skin.

The solvent may be a neutral-smelling solvent. Said neutral-smelling solvents may be used to dilute a perfume composition.

Non-limiting examples of solvents are methanol, ethanol, isopropyl myristate (IPM), tripropylene glycol methyl ether (TMP), dipropylene glycol methyl ether (DPM), diethyl phthalate (DEP) and mixtures thereof.

Without being bound by theory, commonly used emollients or moisturizers are hydrophobic materials that are specially designed to make the external layers of the skin softer and more flexible. Increasing the viscosity of said emollients increases the skin's hydration (water content) by reducing evaporation. Non-limiting examples of emollients include both natural and synthetic such as caprylic/capric triglycerides, isostearyl hydroxystearate, isostearyl isostearate, oils, such as seed oil, fatty acid esters, fatty acid ethers, glycerols, glycols, fatty carbonates, and mixtures thereof. Such materials can be found under the names Labrafac® CC (from Gattefossé), Schercemol™ SHS Ester, Schercemol™ 1818 Ester (from Lubrizol), Florasun® 90 (from Floratech), Cetiol® CC (from BASF).

The hydrophobic composition may comprise sensates. Non-limiting examples of sensates are menthol (L, D, racemic), eucalyptol and eucalyptus oil, peppermint oils, cornmint or arvensis mint oils, spearmint oils, carvone, clove oils, cinnamic aldehyde and cinnamon derivatives, aliphatic carboxamides, ketals, cyclohexyl derivatives, mono-menthyl succinated and mixtures thereof. Some examples are: WS-3 available as ISE 3000 and WS-23 available as ISE 1000 from Qaroma, Inc. MGA available from Symrise, TK10, Coolact available from LIPO Chemicals of Paterson, N.J., and Physcool™.

The composition may be at least partially encapsulated, preferably wherein said encapsulate is selected from core-shell encapsulate, matrix encapsulate and mixtures thereof. In another aspect, the composition is fully encapsulated.

Preferably, the encapsulate is a core-shell encapsulate, more preferably wherein said core-shell encapsulate has a shell material comprising melamine-formaldehyde, an acrylate derived polymer and/or multifunctional acrylates, polyamide, polyurea, polyurethane, polycarbonates, polyvinyl alcohol, acetals (such as 1,3,5-triol-benzene-gluteraldehyde and 1,3,5-triol-benzene melamine), starch, cellulose acetate phthalate and mixtures thereof.

Suitable melamine wall material comprises melamine crosslinked with formaldehyde, melamine-dimethoxyethanol crosslinked with formaldehyde, and mixtures thereof.

Suitable polyacrylate wall material comprises one or more multifunctional acrylate moieties; preferably said multifunctional acrylate moiety being selected from the group consisting of tri-functional acrylate, tetra-functional acrylate, penta-functional acrylate, hexa-functional acrylate, hepta-functional acrylate and mixtures thereof; and optionally a polyacrylate that comprises a moiety selected from the group consisting of an amine acrylate moiety, methacrylate moiety, a carboxylic acid acrylate moiety, carboxylic acid methacrylate moiety and combinations thereof.

The encapsulates may be coated with a deposition aid, a cationic polymer, a non-ionic polymer, an anionic polymer, or mixtures thereof. Suitable polymers may be selected from the group consisting of: polyvinylformaldehyde, partially hydroxylated polyvinylformaldehyde, polyvinylamine, polyethyleneimine, ethoxylated polyethyleneimine, polyvinylalcohol, polyacrylates, chitosan and chitosan derivatives and combinations thereof.

Consumer Product

The composition according to the present invention is comprised in a consumer product, preferably said consumer product being a laundry detergent, an air care product, a liquid fabric enhancer, a solid fabric enhancer, a fabric softener dryer added sheet, in a personal care deodorant product, a personal care body wash/shampoo product, a personal care anti-perspirant product, a dish cleaning product or a skin care product, or a mixture thereof.

Without wishing to be bound by theory, the hydrophobically modified urea ether may be used as a rheology modifier in the consumer product. Alternatively, wherein where the composition is encapsulated or partially encapsulated, the hydrophobically modified urea ether may be used as a rheology modifier in the encapsulate.

The composition may be comprised in a laundry detergent, said laundry detergent comprising a total of, based on total consumer product weight, from 0.01% to 10% of said composition or encapsulated composition and, a material selected from the group consisting of surfactants, builders, chelating agents, dye transfer inhibiting agents, dispersants, enzymes, and enzyme stabilizers, catalytic materials, bleach activators, a fabric softener active, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and mixtures thereof.

The composition may be comprised in an air care product, said air care product comprising a total of, based on total consumer product weight, from 0.01% to 25% of said composition or encapsulated composition and, optionally, one or more materials selected from the group consisting of surfactants, antimicrobial agents, wetting agents, buffering agents, cyclodextrins, propellants, and solvents.

The composition may be comprised in a liquid fabric enhancer, said fabric liquid fabric enhancer comprising a total of, based on total composition weight, from 0.01% to 10% of said composition or encapsulated composition and, a fabric softener active selected from the group consisting of a quaternary ammonium compound, a silicone polymer, a polysaccharide, a clay, an amine, a fatty ester, a dispersible polyolefin, a polymer latex and mixtures thereof.

The composition may be comprised in a fabric enhancer solid particle or bead product comprising from 0.1% to 8% of said composition or encapsulated composition and at least about 25% PEG 8000.

The composition may be comprised in a fabric softener dryer added sheet product, said fabric softener dryer added sheet product comprising from 0.1% to 10% of said composition or encapsulated composition and impregnated onto a non-woven sheet.

The composition may be comprised in a personal care deodorant product, said deodorant product comprising a total of, based on total consumer product weight, from 0.01% to 5% of said composition or encapsulated composition and, optionally, from about 0.01% to about 75% of an antimicrobial, preferably said antimicrobials are selected from the group consisting of metals, zeolites, metal zeolites, quaternary ammonium (quat) compounds (e.g., cetyl pyridinium chloride, and benzylalkonium chloride), quat bound clays, metal bound clays, polyaspirin. salicylic acid, polyvinyl amines, coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulfide, sodium thiosulfate, glycols, diols, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), triclosan, triclocarban, isothiazalinones and azoles, and combinations thereof, more preferably, hexanediol, triclosan, octyl isothiazalinone metals selected from the group consisting of Zn, Cu, Al, Ti, Sn, Bi, and Ag, metal salts selected from the group consisting of zinc carbonate, copper sulfate, and zinc gluconate, metal pyrithione salts selected from the group consisting of ZPT and CuPT, glycols selected from the group consisting of propylene glycol, dipropylene glycol and hexylene glycol and mixtures thereof.

The composition may be comprised in a personal care body wash/shampoo product, said body wash/shampoo comprising a total of, based on total consumer product weight, from 0.01% to 5% of said composition or encapsulated composition and from about 3% to 30% of a surfactant, and, optionally, a micellar phase and/or lamellar phase.

The composition may be comprised in a personal care antiperspirant product, said antiperspirant product comprising a total of, based on total consumer product weight, from 0.01% to 5% of said composition or encapsulated composition and, optionally, from about 1% to about 25% of an aluminum salt antiperspirant active.

The composition may be comprised in a dish cleaning product, said dish cleaning product comprising a total of, based on total consumer product weight, from 0.01% to 2% of said composition or encapsulated composition.

The composition may be comprised in a skin care product, said skin care product comprising a total of, based on total consumer product weight, from 0.1% to 25% of said composition or encapsulated composition.

The consumer product may comprise any mixture thereof.

Methods:

1. Nuclear Magnetic Resonance (NMR) Characterization of the Hydrophobically Modified Urea Ethers $^1$H NMR is used for the characterization of the hydrophobically modified urea ethers. The samples are prepared using $CDCl_3$ (Sigma) as solvent at a concentration of 5-10 mg/mL. They are recorded on a Bruker Avance spectrometer operating at 300 MHz. Spectra are reported in parts per million (ppm) relative to residual chloroform (7.26 ppm).

Hydrophobically modified urea ethers have the following characteristics $^1$H NMR peaks: 1) around 6.0 ppm which corresponds to NH groups of urea, 2) peaks between 3.1-3.9 ppm which corresponds to the methylene protons of polyethylene and polypropylene groups, 3) peaks at 1.1-1.4 ppm corresponding to the $CH_2$ of the end groups ($R_1$) and 4) triplet at 0.8 ppm corresponding to the terminal $CH_3$ group.

$^{13}$C NMR is also used to determine the presence of the carbonyl groups of the urea functionality. The samples are prepared to a concentration of 30 mg/mL using deuterated chloroform (Sigma) as solvent. They are recorded on a Bruker Avance 300 spectrometer at a frequency of 75 MHz. Spectra are also reported in parts per million (ppm) relative to residual chloroform, which is at 77.0 ppm. The characteristic peak for $^{13}$C NMR appears at around 160 ppm, corresponding to C=O group.

To calculate the monomer ratio of copolymer such as the hydrophobically modified urea ethers, $^1$H NMR spectroscopy is a very useful tool. For this method it is important to locate the signal representing each proton. For mixtures of substituted (—$CH_3$ substitution for example) and unsubstituted ether chains, integers can be calculated as follows:

1) Calculate the relative number of moles of propylene glycol (PG). The proton signal that corresponds to $CH_3$ of PG appears at 1.1-1.4 ppm. The signal at this region is overlapping with the $CH_2$ of the end group. Therefore:

Relative number of moles (PG)=[(total proton integration at 1.1-1.4 ppm)−(total number of $CH_2$ protons of end group)]/3 where 3 is the number of methyl protons

2) Calculate the relative number of moles of ethylene glycol (EG). The signals for the methylene protons appear between 3.1-3.9 ppm. These signals represent the protons both from methylene groups of EG and PG. There are three proton signals from PG (CH & $CH_2$ groups) overlapping the EG methylene group in this region. The integral for the three propylene protons is equal to the integral representing the methyl protons (proton integration at 1.1-1.4 ppm−total number of CH$_2$ protons of end group). To determine the molar ratio of the EG units:

Relative number of moles (EG)=[(total proton integration at 3.1-3.9 ppm)−((proton integration at 1.1-1.4 ppm)−(total number of CH$_2$ protons of end group))]/4 where 4 is the number of methylene protons from EG
3) Calculate the mole % of PG (or EG)

mole % of PG (or EG)=relative number of moles of PG (or EG)×100%/(relative number of moles of PG+relative number of moles of EG)

To determine the values of integers for tris-urea ethers $^1$H NMR spectroscopy is used to calculate these values. Similar calculations are used to determine the integers of the substituted or unsubstituted ether moeities:

1) Calculate the integral per proton. For this step it is important to locate the proton signal for the end groups. In the case of the polyether urea derivatives, the end groups are 2 CH$_3$ units and appear clearly at 0.8 ppm.

Integral per proton=proton integration of CH$_3$ groups at 0.8 ppm/6 where 6 is the total number of protons of 2 CH$_3$ end groups
2) Calculate the number of repeat units. The proton signals for ethylene groups appear at 3.1-3.9 ppm.

Number of repeat units=[(total number of proton integration)/(number of methylene protons)]/integral per proton 2. Fourier Transform Infrared (FT-IR) Characterization of the Polyether Urea Derivatives In addition to NMR spectroscopy, FTIR is used to further characterize the hydrophobically modified urea ethers. FTIR offers both quantitative and qualitative analysis of organic, inorganic and polymeric materials. In this case, FTIR is only used to qualitatively determine the absorption spectra. The spectra are recorded neat on a Bruker Vertex 70 spectrometer. The OPUS software package is used to analyze the FTIR spectra. The characteristic peaks for polyether urea derivatives are NH stretch (3300 cm$^{-1}$), C═O (1500-1600 cm$^{-1}$), C—N (1400 cm$^{-1}$) and C—O (1100 cm$^{-1}$).

3. Gel Permeation Chromatography (GPC) Characterization of the Hydrophobically Modified Urea Ethers Without being bound by theory, GPC is one of the most common methods to determine the molecular weight of polymers. GPC samples are prepared using tetrahydrofuran (THF, Sigma) as solvent at a concentration of 5 mg/mL. GPC is performed on a Shimadzu apparatus (UV and RI detection) with a PLgel D column and THF as the eluent at 303 K calibrated with linear polystyrene standards. The values of M$_n$ or M$_w$ for hydrophobically modified urea ethers should fall between the range 1000-7000 Da.

4. Determination of Hydrophobically Modified Urea Ethers in a Hydrophobic Composition.

Hydrophobically modified urea ethers have good solubility in chloroform, therefore extraction with chloroform is performed in order to extract the polyether urea derivative from the composition. First, 10 mL of chloroform (Sigma) is added to 500 mg of the composition. Sonicate the suspension for about 15 minutes using 2012 Branson Ultrasonics CPXH series sonicator at 20-25° C. and gently heat with an oil bath to about 40° C. for 15-20 minutes to ensure that the hydrophobically modified urea ether is extracted. Remove any undissolved solids by filtration or decantation. Collect the filtrate and concentrate it using a rotavap (Buchi rotavapor, 40-45° C., 300 mbar). The concentrate can be characterized by using methods 1-3 ($^1$H NMR, FT-IR and GPC).

An alternative method is to perform dialysis before extraction. Dialysis can be performed with the use of a membrane with molecular weight cut-off of 1000 Da (Spectra/Por®) for about 2-3 days. This will exclude the low molecular weight and the non-polymeric components. After dialysis, extraction with chloroform as described above is performed to further separate the insoluble constituents.

5. Rheology a. Gel strength: An AR-G2 rheometer from TA Instruments is used for rheological measurements. Plate: 40 mm standard steel parallel plate, 300 μm gap. The gel strength is measured using a stress sweep test whereby the oscillation stress is increased from 0.001 to 1000 Pa, taking 10 points per decade at 20° C. and at a frequency of 1 Hz. We take the G' and G" values within the linear viscoelastic region.

b. Viscosity: This parameter is measured using an DHR I from TA Instruments using a 60 mm 1° Cone and a gap size of 52 microns when the viscosity of the fluid is equal or higher than 0.031 Pa·s (31 cPs). The viscosity at a shear rate of 0.1 s$^{-1}$ can be obtained from a logarithmic shear rate sweep from 0.01 s$^{-1}$ to 1000 s$^{-1}$ at 20° C. When fluid viscosity is lower than 0.031 Pa·s (31 cPs), a double wall couette cylinder is used. This geometry consists of an inside cup of 30.2 mm diameter, an inside bob of 31.85 mm diameter, an outside bob of 35 mm diameter and an outside cup of 37 mm diameter. The viscosity of these low viscosity fluids can be obtained from a logarithmic shear rate sweep from 1 s$^{-1}$ to 300 s$^{-1}$ at 20° C.

EXAMPLES

Example 1

Labrafac CC (Caprylic/Capric Triglyceride from Gattefossé) is a universal emollient for oils and emulsions. It improves the feel and spreadability on the skin. Isopropyl Myristate (from Sigma Aldrich) is used in cosmetics where good absorption through the skin is desired and as solvent in perfume compositions, to provide dilution without compromising the olfactory character of the perfume.

At the same time, these materials are highly hydrophobic and difficult to gel.

| | 1A | 1B | 1C | 1D | 1E | 1F |
|---|---|---|---|---|---|---|
| | | | % wt | | | |
| Labrafac CC | 95 | 95 | 97 | | 97 | |
| Isopropyl Myristate | | | | 95 | | 95 |
| C | | | 3 | 5 | | |
| G | 5 | | | | | |
| F | | | | | 3 | 5 |
| High Molecular weight G* | | 5 | | | | |
| G' (Pa) at 1 Hz | 527 | Precipitates, no gel formed | 2726 | 10985 | 59160 | 175363 |
| G" (Pa) at 1 Hz | 40.6 | | 318 | 1175 | 4671 | 6246 |

*
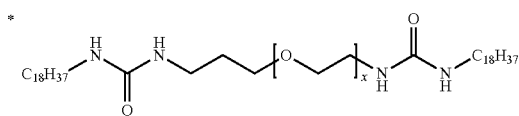

MW = 3991 Da

Non-substituted linear hydrophobically modified urea ethers (comparative examples 1A and 1B), shows that molecular weight for this family of molecules is preferably in the range of 1000 to 3000 Da. Below 1000 Da, hydrophobically modified urea ethers or even the polyetheramine starting materials are soluble and do not form gels neither modify the rheology of the composition. Above 3000 Da, hydrophobically modified urea ethers tend to precipitate upon storage.

When methyl substitutions are included (Examples 1C, 1D, 1E and 1F) rheology properties significantly improve achieving strong gels (G' is always higher then G"). 1F is a really strong gel (high G' values) and has a viscosity of 111 Pa·s (0.1 s$^{-1}$) and a dynamic yield stress of around 8 Pa.

Example 2. Comparative Example Hydrophobically Modified Mono-Urea Versus Bis-Urea

|  | 2A | 2B |
|---|---|---|
|  | % wt | |
| Labrafac CC | 95 | 95 |
| K | 5 | |
| hydrophobically modified mono-urea ether* | | 5 |
| G' (Pa) at 1 Hz | 7134 | 377 |
| G" (Pa) at 1 Hz | 629 | 69 |

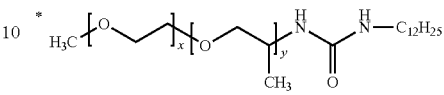

Hydrophobically modified mono-urea ethers provide a lower rheology modification compared to their bis-urea analogs.

Example 3

|  | 3A | 3B | 3C | 3D | 3E | 3F | 3G | 3H |
|---|---|---|---|---|---|---|---|---|
|  | | | | % wt | | | | |
| Labrafac CC | 97 | 97 | 97 | | 95 | 95 | | |
| Isopropyl Myristate | | | | 95 | | | 95 | 95 |
| A | 3 | | | | | | | |
| B | | 3 | | | | | | |
| C | | | 3 | 5 | | | | |
| aromatic A* | | | | | 5 | | 5 | |
| aromatic C** | | | | | | 5 | | 5 |
| G' (Pa) at 1 Hz | 5309 | 5411 | 2726 | 10985 | Dissolves | | Precipitates | |
| G" (Pa) at 1 Hz | 686 | 282 | 318 | 1175 | | | | |
| Viscosity (Pa·s) at 0.1s$^{-1}$ | 15 | 14.5 | 15.4 | | | | | |
| Dynamic Yield stress (Pa) | 0.26 | 0.8 | 1.5 | | | | | |

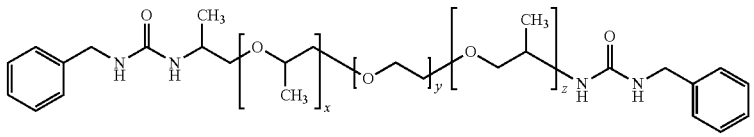

*Aromatic A MW = 866 Da
** Aromatic C MW = 2266 Da

Example 3E, 3F, 3G and 3H are comparative examples: the substitution of aliphatic groups by aromatic ones results in dissolution or precipitation of the hydrophobically modified urea ether.

Example 4. Perfume Gels A to L Provide a Controlled Perfume Release Over Time Compared to the Non-Gelled Perfume Compositions

TABLE 2

| PRM No. | 4A | 4B | 4C | 4D | 4E | 4F | 4G | 4H | 4I | 4J | 4K | 4L |
|---|---|---|---|---|---|---|---|---|---|---|---|---|
| 1 | | | | | | | | 0.5 | | | | |
| 2 | 3.5 | | | | | | | | | | | |
| 3 | 3.5 | | | | | | | | | | | 10 |
| 4 | | | | | | 7.8 | | | | | | |
| 5 | | | | | | | | | | | | 2 |
| 6 | | | | | | | | | | | 0.07 | |

TABLE 2-continued

| PRM No. | 4A | 4B | 4C | 4D | 4E | 4F | 4G | 4H | 4I | 4J | 4K | 4L |
|---|---|---|---|---|---|---|---|---|---|---|---|---|
| 7 | | | | | | | | | | | | |
| 8 | | | | | | | | 2 | | | | |
| 9 | | | | | | | | | | | | 4 |
| 10 | | | | | | | | 1.2 | | | | |
| 11 | 12.5 | 5.5 | | | | | | 3 | | | 3.6 | |
| 12 | | | | | | | | | | | | |
| 13 | | | | | | | | 2 | | | | |
| 14 | | | | | | 0.15 | | | | 1.7 | | |
| 15 | | | | | | | | 0.5 | | | | |
| 16 | | | | | | | | 7 | | | | |
| 17 | | | | 2 | | | 2 | | | | | |
| 18 | | | | 1.8 | | | | | | 4 | | |
| 19 | | | | | | | | | | | | |
| 20 | | | | | | | 4 | | | | | |
| 21 | | | | | | | | | | | | |
| 22 | | | | | | | | | | | 1.8 | |
| 23 | | | | | | | | | | | | |
| 24 | | | | 3.2 | | | 3.8 | | | | | |
| 25 | | | | | | | | | | | | |
| 26 | | | | | | | 13 | | | | | |
| 27 | | | | | | | | | | | | |
| 28 | | | 28 | | | | | | | | | |
| 29 | | | | | | | | | | | | |
| 30 | | | | | | | | | | | | |
| 31 | | | | 13 | | | | | | | | |
| 32 | | 3.6 | | | | 7 | | | | | | |
| 33 | | 17 | | | | 18 | | | | | | |
| 34 | | | | | | | | | | 16 | | |
| 35 | | | | | 9 | | | | | | | |
| 36 | | | | 9 | | | | | | | | |
| 37 | | | 7 | | | | 4 | | | | | |
| 38 | | | 3 | | | | | | | | | |
| 39 | | | | | | | | | | 20 | | |
| 40 | | | | | | | | | | | 12.8 | |
| 41 | | | | | | | | | | | | |
| 42 | | | | | | 8 | | | | | | |
| 43 | | | | | | 5 | | | | 8 | | |
| 44 | | | 6 | | | | | 8 | 2.3 | | | |
| 45 | | | 4 | | | | | | | | | |
| 46 | | | | | | | | | | | | |
| 47 | | | | | | | | | | | | |
| 48 | | | | | | | | | | | | |
| 49 | 1.8 | | | | | | | | | | | 3 |
| 50 | | | | | | 4.8 | | | | | 1.8 | |
| 51 | | | | | | | 2 | | | | | |
| 52 | | | | | | | | 1.7 | | | | |
| 53 | | | | | | 1.8 | | | 5 | | | |
| 54 | | | | | | | | | | | | |
| 55 | | | | | | | | | | | | |
| 56 | | | | | | | | | | | | |
| 57 | | | | | | | | | | | | |
| 58 | | | | 4 | | | | 12.5 | | | | |
| 59 | | | | | | | | | | | 2 | |
| 60 | | | | | | 5.2 | | | | | | |
| 61 | | | | | | | | 5.4 | | 5.1 | | |
| 62 | 3.5 | | | | | | | | | | 3.5 | |
| 63 | 3.5 | | | | | | | | | | | |
| 64 | 5.2 | | 7 | | | | | | | | | |
| 65 | | | | | | | | 5.5 | | | | |
| 66 | 1.7 | | | | | | | 11 | | | 1.6 | 14 |
| 67 | | | | 4 | | | 3.6 | | | | | |
| 68 | | | 7 | | 5 | | | | | 7 | | |
| 69 | | | | 3.2 | | 7 | | | | | | |
| 70 | | | 3.4 | | | | | | | 3 | | |
| 71 | | | | | | | | | | 8 | 5.1 | |
| 72 | | | | | 5 | 4 | | | | | | |
| 73 | | | 3.5 | | | | | 7 | | | | |
| 74 | | | | | | | | 16 | | | | |
| 75 | | | | | | | | | | 1.9 | 3.3 | |
| 76 | 8.6 | 5.4 | | | | | | | | | | 10 |
| 77 | | 4.8 | | | | 9 | | 3.5 | | | | |
| 78 | | | | | | | | | | 5.2 | | |
| 79 | | | | | | | | | | 3.5 | 8.5 | |
| 80 | | | | | | | | | | | | |
| 81 | | | | | | 15 | | | | | | |
| 82 | | | 5.2 | | 11 | | | | | 3.5 | 5.4 | |
| 83 | | | | 2 | | | 1.6 | 7 | | | | |

TABLE 2-continued

| PRM No. | 4A | 4B | 4C | 4D | 4E | 4F | 4G | 4H | 4I | 4J | 4K | 4L |
|---|---|---|---|---|---|---|---|---|---|---|---|---|
| 84 | | 4.2 | | 5.5 | 2.5 | | | | | | | |
| 85 | | | | | | | 0.04 | | | | | |
| 86 | | | | | 6 | | | | | | | |
| 87 | 5.2 | | | | | | | | | | | 2 |
| 88 | | | | | | | 8.6 | | | | | |
| 89 | | | | | 3 | | | | | | | |
| 90 | | | | | | | | 0.1 | | | | |
| 91 | 1.7 | 12 | | | | | | 4 | | | | |
| 92 | | | | | | | | 10 | | | | |
| 93 | | | | 1.6 | | | | | | 4 | | |
| 94 | | | | | 10 | | 1.8 | | 2.5 | | | |
| 95 | | | | | | | | | | | 0.05 | |
| 96 | | | | 0.04 | | 0.05 | | | | | | |
| 97 | | | 0.1 | | | | | | | 0.03 | | |
| 98 | 0.05 | | | | | | | | | | | |
| 99 | | | | | 6 | | | | 2.3 | | | |
| 100 | | | | | | 10 | 3.6 | | | | | |
| 101 | | 11 | | | | | | | | | | 1 |
| 102 | | | | | | | | | 3.5 | | | |
| 103 | | | | | | | | | | | | |
| 104 | | | | | | | | | | 11 | 3.6 | |
| 105 | | 5 | | | 4 | | | 2.3 | | | | 4 |
| 106 | | 15 | | | | | | | | | | 8 |
| 107 | | 3.3 | | | 7 | | | 1.8 | | | | 4 |
| 108 | | 7 | | | 7.5 | | | 1.8 | | | | 2.5 |
| 109 | | | 0.2 | | | | | | | | | 8 |
| 110 | | 11.7 | | | 4.5 | | | 5.6 | | | | 3.5 |
| 111 | | 6.5 | | | 3 | | | 3.4 | | | | 4 |
| 112 | | 2.7 | | | 6 | | | 2.5 | | | | 2 |
| 113 | | 2.5 | | | | | | | | | | 7 |
| 114 | | 3 | | | 3 | | 3.2 | | 1.2 | 3.4 | | |
| 115 | | | | 1.4 | | | | | | | | 6 |
| Labrafac CC | | | | | | | | | 51.9 | | 43.95 | |
| IPM | | | | | | | 37.36 | | | | | |
| TMP | | | | 39.26 | | | | | | | | |
| DPM | 47.25 | | | | | | | | | | | |
| I | 2 | 3.4 | 2 | | | 3 | | | 5 | | 3 | |
| J | | | 5 | 2.7 | | 4.5 | 3 | | | 3.5 | | 5 |

Example 4C has a G' of 1800 Pa, G" of 400 Pa and a dynamic yield stress of 0.5 Pa.

Example 5

|  | 5A | 5B |
|---|---|---|
|  |  | % wt |
| Labrafac CC | 97 | |
| Isopropyl Myristate | | 95 |
| I | 3 | 5 |
| G' (Pa) at 1 Hz | 140 | 216318 |
| G" (Pa) at 1 Hz | 24.9 | 12373 |
| Viscosity (Pa · s) at 0.1 s$^{-1}$ | 10.3 | |
| Dynamic Yield stress (Pa) | 0.08 | |

Example 6

|  | 6A | 6B |
|---|---|---|
|  |  | % wt |
| Labrafac CC | 97 | |
| Isopropyl Myristate | | 99 |
| L | 3 | 1 |
| G' (Pa) at 1 Hz | 509 | |
| G" (Pa) at 1 Hz | 86 | |

-continued

|  | 6A | 6B |
|---|---|---|
|  |  | % wt |
| Viscosity (Pa · s) at 0.1 s$^{-1}$ | 60 | |
| Dynamic Yield stress (Pa) | 7 | |

Example 7

25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of the composition of example 4G, previously heated to about 50° C. is added to the previous mixture under mechanical agitation and the temperature of the mixture is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 85° C. and maintained overnight with continuous stirring to complete the encapsulation process.

Example 8. Fabric Spray Compositions

An Air Care product is prepared with composition according to invention.

| Ingredient | % wt Active | | |
|---|---|---|---|
| | A | B | C |
| Tween 20 | 1.00 | 1.00 | 1.00 |
| Surfynol 465 | 0.059 | 0.059 | 0.059 |
| Surfynol 104PG | 0.020 | 0.020 | 0.020 |
| Arquad HTL8 | 0.49 | 0.49 | 0.49 |
| Permethyl 102A | 0.1979 | NIL | NIL |
| Triethanolamine | 0.30 | 0.30 | 0.30 |
| Triethanolamine HCL | 0.012 | 0.012 | 0.012 |
| Koralone B-119 | 0.01 | 0.01 | 0.01 |
| Xanthan gum | 0.15 | | |
| Composition according to example 7 | 0.8 | | |
| Composition according to example 4C | | 1.5 | |
| Composition according to example 4E | | | 0.3 |
| Water | Balance to 100 | Balance to 100 | Balance to 100 |
| Formula pH | 8.6 | 8.6 | 8.6 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumer product composition comprising:
   a) a hydrophobic material; and
   b) from about 0.1% to about 10% by weight of the composition of a hydrophobically modified urea ether having the following structure:

$$R_1-N(H)-C(O)-N(H)-L-N(H)-C(O)-N(H)-R_2 \quad (I)$$

wherein $R_1$, $R_2$ and L are selected from the group consisting of substituted or unsubstituted aliphatic carbon chain, substituted or unsubstituted polyether chain and mixtures thereof;

with the proviso that at least one $R_1$, $R_2$ or L contains an ether moiety;

and wherein the hydrophobically modified urea ether has a molecular weight from about 1100 to about 3500 Da.

2. The consumer product composition according to claim 1, wherein in the hydrophobically modified urea ether, L has the formula $$-A_a-B_b-C_c-D_d- \quad (II)$$

wherein, a, b, c and d are integers independently selected from about 0 to about 40 and (a+b+c+d) is from about 3 to about 132; and A, B, C, D are independently selected from the group consisting of:

[structures shown]

wherein R, S, $T_1$, $T_2$, V are independently selected from the group consisting of:

—H, —CH$_3$, —CH$_2$CH$_3$,

[structure shown]

wherein W is —H or —CH$_3$, w is an integer from about 1 to about 30 and $R_3$ is a substituted or unsubstituted aliphatic carbon chain from about 8 to about 20 carbons.

3. The consumer product composition according to claim 1, wherein in the hydrophobically modified urea ether, $R_1$ and $R_2$ are independently selected from the group consisting of

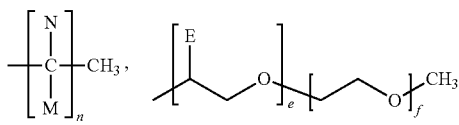

wherein;

N, M and E are independently selected from the group consisting of —H, —CH$_3$, —CH$_2$CH$_3$;

n is an integer from about 8 to about 20; and e and f are integers independently selected from about 0 to about 30, and (e+f) is from about 1 to about 30.

4. The consumer product composition according to claim 2, wherein in the hydrophobically modified urea ether, R$_1$, R$_2$ and R$_3$ are the same.

5. The consumer product composition according to claim 1, wherein in the hydrophobically modified urea ether, the polyether chain is partially substituted.

6. The consumer product composition according to claim 1, wherein the hydrophobic material is a perfume raw material, an emollient, a solvent, anti-bacterial, sensate or mixtures thereof.

7. The consumer product composition according to claim 6, wherein the hydrophobic material is a perfume composition comprising perfume raw materials, solvents or mixtures thereof.

8. The consumer product composition according to claim 1, wherein said composition is at least partially encapsulated.

9. The consumer product composition according to claim 8, wherein said encapsulate is selected from core-shell encapsulate, matrix encapsulate or mixtures thereof.

10. The consumer product composition according to claim 9, wherein said encapsulate is a core-shell encapsulate, wherein the shell material of said core-shell encapsulate comprises melamine-formaldehyde, an acrylate derived polymer and/or multifunctional acrylates, polyamide, polyurea, polyurethane, polycarbonates, polyvinyl alcohol, acetals, starch, cellulose acetate phthalate or mixtures thereof.

11. The consumer product of claim 10, said consumer product being selected from the group consisting of:

a. a laundry detergent, said laundry detergent comprising a total of, based on total consumer product weight, from about 0.01% to about 10% by weight of said composition according to claim 7 and, a material selected from the group consisting of surfactants, builders, chelating agents, dye transfer inhibiting agents, dispersants, enzymes, and enzyme stabilizers, catalytic materials, bleach activators, a fabric softener active, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, carriers, structurants, hydrotropes, processing aids, solvents, pigments and mixtures thereof;

b. an air care product, said air care product comprising a total of, based on total consumer product weight, from 0.01% to 25% by weight of said composition according to claim 7 and, optionally, one or more materials selected from the group consisting of surfactants, antimicrobial agents, wetting agents, buffering agents, cyclodextrins, propellants, and solvents;

c. a liquid fabric enhancer, said fabric liquid fabric enhancer comprising a total of, based on total composition weight, from about 0.01% to about 10% by weight of said composition according to claim 7 and, a fabric softener active selected from the group consisting of a quaternary ammonium compound, a silicone polymer, a polysaccharide, a clay, an amine, a fatty ester, a dispersible polyolefin, a polymer latex and mixtures thereof;

d. a fabric enhancer solid particle or bead product comprising from about 0.1% to about 8% by weight of said composition according to claim 7 and at least 25% by weight of PEG 8000;

e. a fabric softener dryer added sheet product, said fabric softener dryer added sheet product comprising from about 0.1% to about 10% by weight of said composition according to claim 7 and impregnated onto a non-woven sheet;

f. a personal care deodorant product, said deodorant product comprising a total of, based on total consumer product weight, from about 0.01% to about 5% by weight of said composition according to claim 7 and, optionally, from about 0.01% to about 75% by weight of an antimicrobial;

g. a personal care body wash/shampoo product, said body wash/shampoo product comprising a total of, based on total consumer product weight, from about 0.01% to about 5% by weight of said composition according to claim 7 and from about 3% to about 30% by weight of a surfactant, and, optionally, a micellar phase and/or lamellar phase;

h. a personal care antiperspirant product, said antiperspirant product comprising a total of, based on total consumer product weight, from about 0.01% to about 5% by weight of said composition according to claim 7 and, optionally, from about 1% to about 25% by weight of an aluminum salt antiperspirant active;

i. a dish cleaning product, said dish cleaning product comprising a total of, based on total consumer product weight, from about 0.01% to about 2% by weight of said composition according to claim 7;

j. a skin care product, said skin care product comprising a total of, based on total consumer product weight, from about 0.1% to about 25% by weight of said composition according to claim 7; and k. a mixture thereof.

12. A consumer product composition comprising:

a) a hydrophobic material; and b) from about 0.1% to about 10% by weight of the composition of a hydrophobically modified urea ether having the following structure:

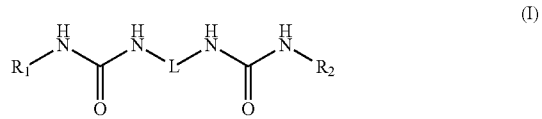

(I)

wherein R$_1$, R$_2$ and L are selected from the group consisting of substituted or unsubstituted aliphatic carbon chain, substituted or unsubstituted polyether chain and mixtures thereof;

with the proviso that at least one R$_1$, R$_2$ or L contains an ether moiety;

and wherein the hydrophobically modified urea ether has a molecular weight from about 1000 to about 7000 Da, wherein in the hydrophobically modified urea ether, $R_1$ and $R_2$ are independently selected from the group consisting of

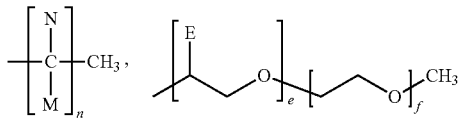

wherein;

N, M and E are independently selected from the group consisting of —H, —CH$_3$, —CH$_2$CH$_3$;

n is an integer from about 8 to about 20; and e and f are integers independently selected from about 0 to about 30, and (e+f) is from about 1 to about 30.

13. A consumer product according to claim 12, wherein the hydrophobically modified urea ether has a molecular weight from about 1100 to about 3500 Da.

14. The consumer product composition according to claim 12, wherein the hydrophobic material is a perfume raw material, an emollient, a solvent, anti-bacterial, sensate or mixtures thereof.

15. The consumer product composition according to claim 1, wherein said composition is at least partially encapsulated.

16. A consumer product composition comprising:
a) a hydrophobic material; and
b) from about 0.1% to about 10% by weight of the composition of a hydrophobically modified urea ether having the following structure:

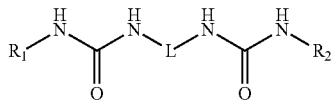

wherein $R_1$, $R_2$ and L are selected from the group consisting of substituted or unsubstituted aliphatic carbon chain, substituted or unsubstituted polyether chain and mixtures thereof;

with the proviso that at least one $R_1$, $R_2$ or L contains an ether moiety;

and wherein the hydrophobically modified urea ether has a molecular weight from about 1000 to about 7000 Da, wherein in the hydrophobically modified urea ether, L has the formula -A$_a$-B$_b$-C$_c$-D$_d$-     (II)

wherein, a, b, c and d are integers independently selected from about 0 to about 40 and (a+b+c+d) is from about 3 to about 132; and A, B, C, D are independently selected from the group consisting of:

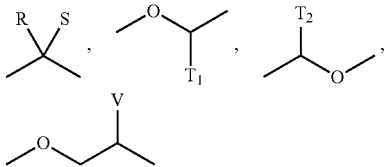

wherein R, S, T$_1$, T$_2$, V are independently selected from the group consisting of:

—H,   —CH$_3$,   —CH$_2$CH$_3$,

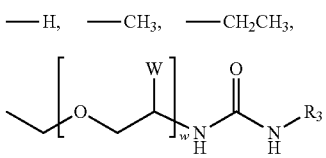

wherein W is —H or —CH$_3$, w is an integer from about 1 to about 30 and $R_3$ is a substituted or unsubstituted aliphatic carbon chain from about 8 to about 20 carbons, wherein $R_1$, $R_2$ and $R_3$ are the same.

17. A consumer product according to claim 16, wherein the hydrophobically modified urea ether has a molecular weight from about 1100 to about 3500 Da.

18. The consumer product composition according to claim 16, wherein the hydrophobic material is a perfume raw material, an emollient, a solvent, anti-bacterial, sensate or mixtures thereof.

19. The consumer product composition according to claim 16, wherein said composition is at least partially encapsulated.

* * * * *